US006159680A

United States Patent [19]
Parada et al.

[11] Patent Number: 6,159,680
[45] Date of Patent: *Dec. 12, 2000

[54] ASSAY FOR PHARMACOLOGICAL AGENTS THAT BLOCK NEUROFIBROMIN ACTION

[75] Inventors: Luis F. Parada; Kristine S. Vogel, both of Dallas, Tex.

[73] Assignee: Board of Regents, The University of Texas System, Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/499,419

[22] Filed: Jul. 7, 1995

[51] Int. Cl.[7] .............................. C12N 5/00; C12N 15/00; C12N 15/63; C12N 15/09
[52] U.S. Cl. ................................. 435/4; 435/6; 435/69.1; 435/325; 435/455; 435/463; 800/18
[58] Field of Search .......................... 514/44; 435/240.2, 435/69.1, 6, 4, 325, 455, 463; 935/1, 19, 34, 36, 37, 38; 536/23.1, 23.5; 800/18

[56] References Cited

U.S. PATENT DOCUMENTS

| | | | |
|---|---|---|---|
| 5,196,333 | 3/1993 | Chalfie et al. | 435/240.1 |
| 5,227,292 | 7/1993 | White et al. | 435/69.1 |
| 5,527,682 | 6/1996 | Owens et al. | 435/6 |

FOREIGN PATENT DOCUMENTS

WO 92/00387 1/1992 WIPO.
WO 94/28009 12/1994 WIPO.

OTHER PUBLICATIONS

Adams et al., "NF1–L is the DNA–Binding Component of the Protein Complex at the Peripherin Negative Regulatory Element," *The Journal of Biological Chemistry*, 270(12):6975–6983, Mar. 1995.

Baizer et al., "Regulated Expression of the Neurofibromin Type I Transcript in the Developing Chicken Brain," *Journal of Neurochemistry*, 61(6):2054–2060, 1993.

Huynh et al., "Expression of Neurofibromin, the Neurofibromatosis 1 Gene Product: Studies in Human Neuroblastoma Cells and Rat Brain," *Neuroscience Letters*, 143:233–236, 1992.

Koh et al., "Potentiated Necrosis of Cultured Cortical Neurons by Neurotrophins," *Science*, 268:573–575, Apr. 1995.

Orkin et al., Report and Recommendations of the Panel to Assess the NIH Investment in Research on Gene Therapy, Dec. 7, 1995.

Gura, Science, vol. 270, pp. 575–577, Oct. 27, 1995.

Brannan et al., Genes and Development, vol. 8, pp. 1019–1029, May 1, 1994.

Ballester et al., Cell, vol. 63, pp. 851–859, Nov. 16, 1990.

Kamal et al., Journal of Biological Chemistry, vol. 268, pp. 22331–22337, Oct. 25, 1993.

Vogel et al., Cell, vol. 82, pp. 733–742, Sep. 8, 1995.

Moreadith et al., Journal of Molecular Medicine, vol. 75, pp. 208–216, 1997.

*Primary Examiner*—Jasemine Chambers
*Assistant Examiner*—Jill D. Martin

[57] ABSTRACT

A targeted disruption of the NF1 gene in mice has been used to demonstrate that both neural crest- and placode-derived sensory neurons isolated from NF1(–/–) embryos develop, extend neurites, and survive in the absence of neurotrophins, whereas their wild-type counterparts die rapidly unless NGF or BDNF is added to the culture medium. Moreover, NF1 mutant sympathetic neurons survive for extended periods and acquire mature morphology in the presence of NGF-blocking antibodies. The discovery is useful in screening candidate substances for inhibition of neurofibromin action and in therapy for neurodegeneration due to disease or trauma.

20 Claims, 11 Drawing Sheets

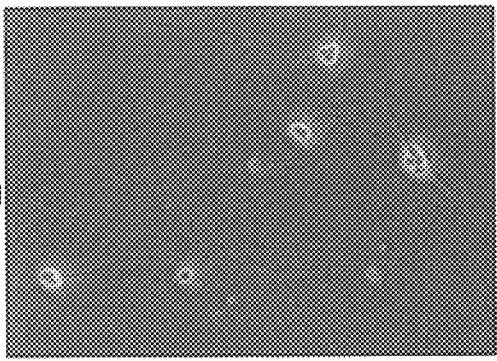
FIG. 9A
FIG. 9B
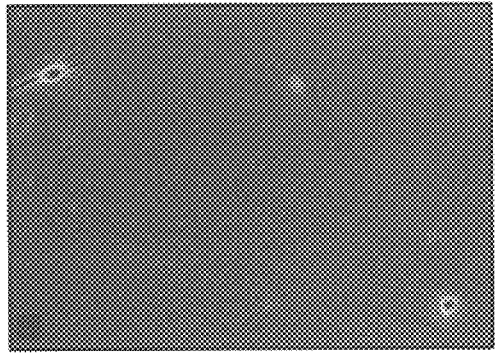
FIG. 9C
FIG. 9D

may directly activate proteins that regulate ras, including guanine nucleotide exchange factor and GAP (Li et al., 1992).

ASSAY FOR PHARMACOLOGICAL AGENTS THAT BLOCK NEUROFIBROMIN ACTION

BACKGROUND OF THE INVENTION

The government owns rights in the present invention pursuant to grant number N01-C0-74101 with ABL.

1. Field of the Invention

The present invention relates generally to the fields of neurophysiology and neuropharmacology and more particularly to the action of neurofibromin-1 and its role in the survival of neural cells in the absence of neurotrophins.

2. Description of the Related Art

In humans, mutations in the neurofibromatosis 1 (NF1) gene lead to benign and malignant tumors of the peripheral nervous system and to abnormal distributions of melanocytes (Riccardi 1991; Gutmann and Collins, 1993). The common embryonic origin of these cell populations is the neural crest (Weston, 1970). The product of the NF1 gene, neurofibromin, is a 250 kDa protein that is widely expressed during embryogenesis (Daston and Ratner, 1992; Huynh et al., 1994). In the embryonic mouse dorsal root ganglia and CNS, increases in neurofibromin mRNA and protein coincide with periods of neuronal differentiation (Huynh et al., 1994). In the adult rodent, the brain and spinal cord are the predominant sites of neurofibromin expression (Daston et al., 1992).

Neurofibromin contains a 350-amino acid domain that has homology to mammalian (GAP) and yeast (IRA) GTPase-activating proteins that function as negative regulators of the p21ras oncoprotein (Ballester et al., 1990; Buchberg et al., 1990; Martin et al., 1990; Xu et al., 1990a). This GAP-related domain (GRD) of human neurofibromin can complement loss of IRA function and activate ras-GTPase in yeast (Ballester et al., 1990; Xu et al., 1990b). In addition, neurofibromin may regulate p21 ras activity independently of its GTPase-activating properties, as overexpression of neurofibromin can inhibit growth of cells transformed by the v-Ha-ras oncogene, which is resistant to GTPase stimulation (Johnson et al., 1994).

p21ras has been implicated in the neurotrophin response for embryonic vertebrate sensory and sympathetic neurons. During development, these neurons become dependent on specific neurotrophins for survival as they contact their targets and gain access to these molecules (reviewed by Korsching, 1993; Davies, 1994; Vogel, 1994). Nerve Growth Factor stimulates activation of p21 ras in embryonic chick dorsal root ganglion neurons (Ng and Shooter, 1993). Moreover, ectopic expression of activated p2lras protein can mimic the survival and neurite-promoting effects of neurotrophins in embryonic chick sensory neurons and in rat PC12 pheochromocytoma cells (D'Arcangelo and Halegoua, 1993). Conversely, in a more direct experiment, introduction of function-blocking ras antibodies abrogates the effects of neurotrophins on these neurons (Borasio et al., 1989; 1993).

NGF and its related neurotrophins: BDNF, NT-3, and NT4/5, bind cell surface tyrosine kinase receptors (TrkA, TrkB, and TrkC; reviewed by Snider, 1994). In rat pheochromocytoma (PC12) cells, NGF-mediated tyrosine phosphorylation of TrkA stimulates intracellular signalling pathways that are known to include activation of SHC, PLC-gammal, PI-3 kinase, and MAP kinases (Kaplan and Stephens, 1994). This body of results is consistent with the idea that the ras pathway is important, and may be essential, in neurotrophin/trk mediated signalling. Thus, trk receptors may directly activate proteins that regulate ras, including guanine nucleotide exchange factor and GAP (Li et al., 1992).

In addition, neurotrophins have been identified as affecting various neurodegenerative diseases and neurotrophin are administered therapeutically. For example, microencapsulated BDNF and other trophic factors have been suggested as a possible therapy of neurodegenerative disorders, in particular for peripheral neuropathies and CNS disorders where supplementation of neurotrophins retards or even prevents neural degeneration (Mittal et al., 1994). Neurotrophic factors have also been suggested for the prevention or delay of age related neurodegeneration or Alzheimer's disease (Rylett and Williams, 1994). Neurotrophic factors may also be used in the treatment of stroke, ischemia or other nervous system injury (Olson, 1993), amyotrophic lateral sclerosis (ALS) (Seeburger and Springer, 1993) as well as Parkinson's Disease, Huntington's Disease and spinal chord injuries.

However, the use of neurotrophins suffers from several drawbacks. For example, neurotrophins are unstable in vivo and high concentrations are needed in order to produce the desired effects. Unfortunately, high concentrations of neurotrophins may cause undesirable secondary effects. In addition, the mechanisms of sequestration of neurotrophic factors is unknown. Also the use of neurotrophins depends on a functional receptor, and because the receptor may be located at the axonal end of the neural cell, the receptor may be missing or damaged, especially in trauma or spinal chord injury. There still exists therefore a need for a method of therapy that prevents or delays neural cell degeneration due to neurodegenerative disease or other trauma.

SUMMARY OF THE INVENTION

The present invention overcomes these drawbacks by providing methods of developing therapies for neurodegenerative disease or trauma that do not rely on the administration of neurotrophic factors. The invention arises from the discovery that neural cells that lack neurofibromin-1 (NF-1) activity are able to survive without the addition of neurotrophic factors, and therefore, nerve cell damage or death that occurs in disease or trauma that disrupts the neurotrophin-activated cascade of events may be delayed or prevented by inhibiting NF-1 activity in the neural cell.

An embodiment of the present invention is an isolated neural cell, wherein said neural cell is capable of survival, in culture, in the absence of neurotrophin factors, and more preferably wherein the neuron has a mutation in the neurofibromin-1 (NF1) gene. The NF1 gene is described as that nucleic acid sequence identified in patent application WO 92/00387 and U.S. Pat. No. 5,227,292, both incorporated herein by reference.

In certain embodiments, the invention may be described as a method of identifying a substance that blocks neurofibromin action. The method comprises the steps of:

(a) obtaining a substance suspected of blocking neurofibromin action;

(b) obtaining a culture of neural cells;

(c) determining the survival of said neural cells in the presence of said substance and in the absence of neurotrophic factors;

(d) determining the survival of the neural cells of claim 1 under identical conditions as in step (c), except in the absence of said substance; and (e) determining the survival of the neural cells of claim 1 under identical conditions as in step (c);

wherein said substance has no effect on survival of neural cells of steps (d) and (e); and wherein said substance enhances survival of neural cells of step (c) when compared to survival of said neural cells of step (c) in absence of said substance, is indicative of blocking neurofibromin action. The neural cells may be nodose, trigeminal, dorsal root ganglion (DRG), or SSG cells.

The method may further comprise the step of determining the effect of the presence of said substance on yeast IRA or mammalian GAP protein activity. It is contemplated that a preliminary screening of a candidate substance may be done in a yeast cell to determine the effect of the candidate substance on the activity of the IRA gene product, or the effect on the mammalian GAP protein (Bollag and McCormick, 1991, incorporated herein by reference).

An embodiment of the present invention is also a method of preventing neural cell death, comprising blocking neurofibromin action in a neural cell. In preferred embodiments, the neurofibromin action is blocked by contacting the cell with a substance that blocks neurofibromin action, or the neurofibromin action may be blocked by a neurofibromin-1 antisense nucleic acid sequence that is delivered to the neural cell. Delivery may be by adenoviral vector, herpes viral vector, or by any other acceptable means such as liposome delivery systems, for example.

An embodiment of the invention is also a method of preventing neural cell death comprising contacting said neural cell with a substance that inhibits neurofibromin activity, and wherein the substance is identified by the method described above as comprising the steps of:

(a) obtaining a substance suspected of blocking neurofibromin action;
(b) obtaining a culture of neural cells;
(c) determining the survival of said neural cells in the presence of said substance and in the absence of neurotrophic factors;
(d) determining the survival of the neural cells of claim 1 under identical conditions as in step (c), except in the absence of said substance; and
(e) determining the survival of the neural cells of claim 1 under identical conditions as in step (c);
wherein said substance has no effect on survival of neural cells of steps (d) and (e); and wherein said substance enhances survival of neural cells of step (c) when compared to survival of said neural cells of step (c) in absence of said substance, is indicative of blocking neurofibromin action. The neural cells may be nodose, trigeminal, dorsal root ganglion (DRG), or SSG cells.

BRIEF DESCRIPTION OF THE DRAWINGS

FIG. 9A. NF1 mutant sympathetic neurons survive and extend neurites in the absence of neurotrophins. E13.5 SCG neurons, NF1(−/−), 6 days in vitro, no neurotrophins (200×).

FIG. 9B. E13.5 SCG neurons, NF1(−/−), 6 days in vitro, NGF 1 ng/ml (200×).

FIG. 9C. E13.5 SCG neurons, NF1(−/−), 21 days in vitro, no neurotrophins (200×).

FIG. 9D. E13.5 SCG neurons, NF1(+/−), 21 days in vitro, NGF 1 ng/ml (200×).

DETAILED DESCRIPTION OF THE PREFERRED EMBODIMENTS

Figure 1:
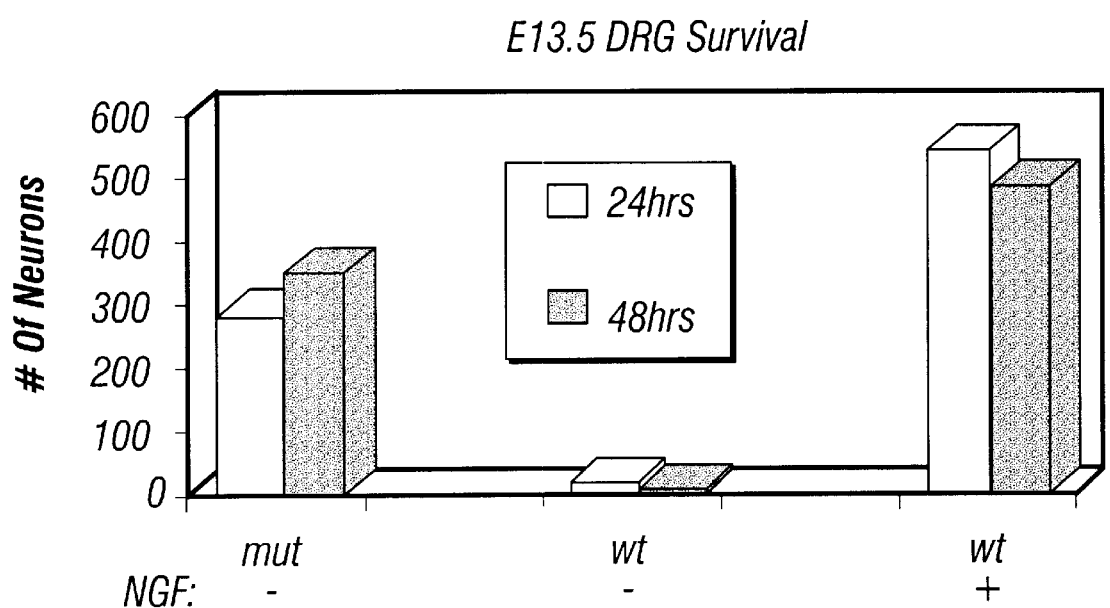
FIG. 1. NF1 mutant DRG neurons survive in the absence of NGF. Replicate cultures were established from stage-matched NF1 mutant and wild-type embryos; NGF was added to wild-type cultures 6 hours after plating at a concentration of 1 ng/ml. Similar results were obtained with DRG taken from mutant and wild-type embryos from 2 additional litters. For the NF1 mutant cultures, the range of values at 24 hours is 272–298 neurons and at 48 hours 307–376 neurons. For wild-type cultures in the presence of NGF, the range of values at 24 hours is 490–578 neurons and at 48 hours 433–554 neurons.
Figure 2A:
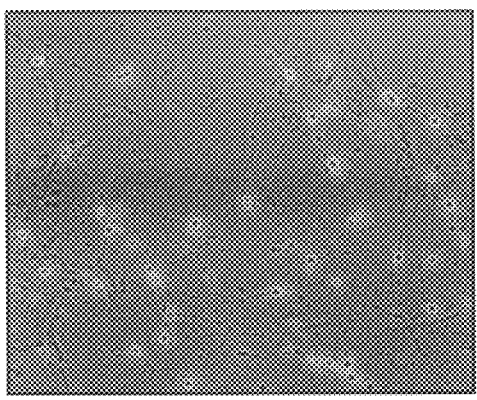
FIG. 2A. NF1 mutant DRG neurons survive and extend neurites in the absence of neurotrophins. E13.5 DRG neurons isolated from NF1(−/−) embryo, 108 hours in vitro, no neurotrophins (100×).
Figure 2B:
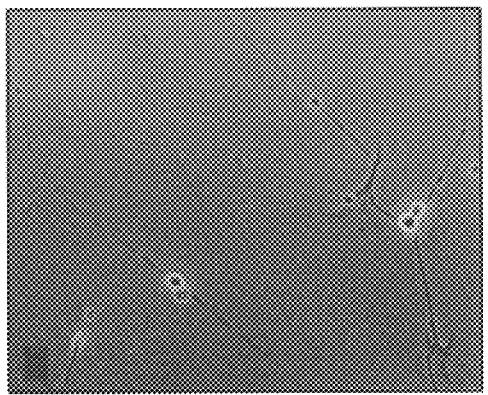
FIG. 2B. E13.5 DRG neurons isolated from NF1(−/−) embryo, 72 hours in vitro, no neurotrophins (200×).
Figure 2C:
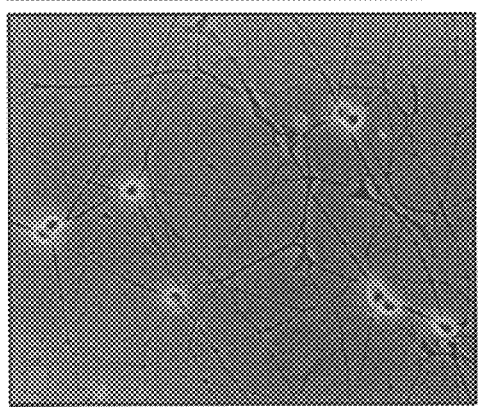
FIG. 2C. E13.5 DRG neurons isolated from NF1(+/−) embryo, 72 hours in vitro, NGF 2 ng/ml (200×).
Figure 2D:
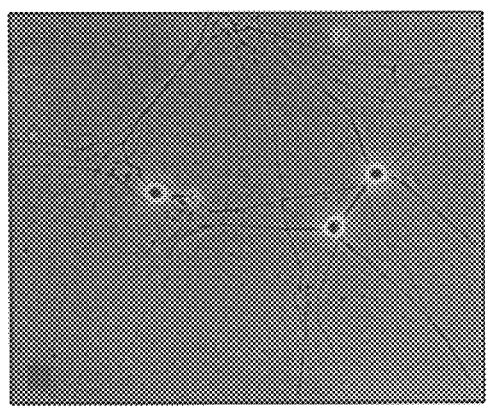
FIG. 2D. E13.5 DRG neurons isolated from NF1(−/−) embryo, 72 hours in vitro, NGF 2 ng/ml (200×).

Neurons in the mature vertebrate nervous system require constant stimulation from trophic (survival) factors to remain alive. Any interference with this signalling mechanism can result in the default process of programmed cell death. A further feature of neurons is that, once hard wired, these cells are terminally differentiated and incapable of dividing. Replacement of functionally distinct neuronal populations lost to injury or disease is unlikely or impossible since few if any stem cells are available in the brain and spinal cord to replenish neurons that die.

Since many of the genes that mediate trophic or survival signalling are now identified, it seems likely that mutation of these genes is not the primary cause in the etiology of the most common genetic neuromuscular disorders. Through mutational analysis in mice, it is known that defects in these neurotrophic factor and receptor genes as well as their downstream effectors would not permit the organism to survive. However, one frequent underlying feature in neurodegenerative disorders (i.e., ALS, Huntington's, Alzheimer's) or in trauma such as spinal cord injury, is the disruption (mechanical, genetic or enzymatic) of the survival signalling mechanism in neurons. This disruption is believed to play a significant role in resultant neuronal deterioration. Experimental paradigms provide evidence that neurotrophins may normally function as neuroprotective agents under conditions of stress. It is therefore possible that manipulation of the survival pathways in neurons may permit compensation for neuronal damage of diverse origin.

The present discovery arises from the observation that the product of the Neurofibromatosis Type I gene, neurofibromin, is mechanistically linked to the cellular pathway required for neuronal survival in vertebrate neurons. More precisely, neurofibromin is a negative regulator of the neurotrophin signalling pathway. Hence, in the normal state, neurotrophin binding to trk receptors on the cell surface initiates a signalling cascade that overcomes the negative control of neurofibromin and leads to neuronal survival. In the absence of neurotrophins, the action of neurofibromin insures that no leaky transmission of survival signalling occurs. In the absence of neurofibromin function, leakiness of the signalling pathway is permitted and neurons survive even in the absence of neurotrophic factors. Therefore, primary neuronal cultures which normally depend on neurotrophins for survival, can be used to test strategies that inactivate the function of neurofibromin and thus permit survival in the absence of neurotrophins.

Mouse embryos homozygous for a null allele of the NF1 gene die at 13.5 d.p.c. and exhibit several abnormalities of neural crest-derived tissues (Brannan et al., 1994; Jacks et al., 1994). This targeted disruption of the NF1 gene has been exploited in the mouse (Brannan et al., 1994) to examine the role of neurofibromin in the development of neurotrophin-responsiveness in sensory and sympathetic neurons. Sensory neurons of the trigeminal (TG), dorsal root (DRG), and nodose (ND) ganglia contact their central and peripheral targets and acquire mature patterns of neurotrophin dependence prior to E13.5, when NF1(−/−) embryos die (Buchman and Davies, 1993; Davies et al., 1994, K.S.V. and L.F.P., unpublished). This sequence of events has permitted the investigation of the development of peripheral neurons in the NF1 mutant embryos. The present disclosure shows that most NF1 mutant DRG and TG neurons, which normally require NGF for survival, and ND neurons, which normally require BDNF, can survive for extended periods in primary culture in the absence of exogenous neurotrophins. Sympathetic neurons of the superior cervical ganglion (SCG) have not contacted their targets nor acquired mature patterns of neurotrophin dependence by the time of targeted NF-1 embryonic death at E13.5 (Coughlin and Collins, 1985; Rubin, 1985); however, SCG neurons isolated from normal E13.5 mice respond to NGF with increased survival after a period of 48 hours in culture. Furthermore, it is shown that E13.5 SCG neurons isolated from NF1 mutant embryos survive for weeks in the absence of NGF. These results are consistent with an essential role for neurofibromin in the establishment of neurotrophin dependence in both sensory and sympathetic neurons and provides new insight into the possible mechanisms of disease in von Recklinghausen's neurofibromatosis.

Sensory neurons in cranial and dorsal root ganglia arise from migratory cells of the placodal ectoderm and neural crest (reviewed by Teillet et al., 1992; Vogel, 1992). After localizing in the regions of the developing ganglia, sensory neuronal precursors proliferate and ultimately undergo their terminal mitosis, or "neuron birthday". Sensory neurons subsequently express differentiated neuronal traits and extend axons to their central and peripheral targets. During this period of initial target contact, sensory neurons begin to acquire dependence on target-derived neurotrophins for survival and maintenance of differentiated traits (reviewed by Vogel, 1994). As target innervation is established, sensory neurons undergo a period of programmed cell death, whereby superfluous and inappropriately connected neurons are eliminated (reviewed by Oppenheim, 1991).

As disclosed herein, trigeminal, nodose, and dorsal root ganglion sensory neurons that lack neurofibromin differ dramatically from their normal counterparts in at least one aspect of neuronal development: acquisition of neurotrophin dependence. In the mouse, neuronal precursors in the trigeminal and nodose ganglia have ceased proliferating by E12.5; neuron birthdays in the DRG are over by E13.5 (Lawson and Biscoe, 1979). Trigeminal and DRG neurons isolated from normal embryos at these stages require NGF for survival and neurite outgrowth in vitro, while nodose neurons require BDNF (Buchman and Davies, 1993; Davies et al., 1993). However, most sensory neurons isolated from NF1(−/−) embryos at these stages survive and extend neurites in vitro in the absence of neurotrophins. Although subpopulations of NF1 mutant trigeminal (E12.5) and DRG (E13.5) neurons isolated during the period of maturation respond to NGF with increased survival, no such NGF-responsive neurons can be found in trigeminal and dorsal root ganglia isolated from younger NF1(−/−) embryos. In contrast, many trigeminal and DRG neurons isolated from young wild-type littermates acquire dependence on NGF for survival after a few days in vitro. Similar results were obtained with NF1 mutant nodose neurons, which are normally dependent on BDNF for survival.

Autocrine and Paracrine Effects.

Since some ganglion cultures contained glial cells and neuronal precursors in addition to postmitotic neurons, it was important to establish that the loss of neurofibromin had a direct effect on neuron survival. To accomplish this, the survival of individual sensory neurons was monitored in very low density cultures (Vogel and Davies, 1991) and as single, isolated cells over a period of several days. In both conditions, dorsal root and nodose ganglion neurons isolated from NF1 mutant embryos survived for several days in the absence of neurotrophins and survival factors produced by other cells. Moreover, medium conditioned by NF1 mutant DRG cells failed to support the survival of wild-type neurons. These results are most consistent with a direct role for neurofibromin in signal transduction pathways involved in the neurotrophin-dependent survival of embryonic sensory neurons.

Sympathetic neurons in the SCG arise from sympathoadrenal precursors derived from the neural crest (reviewed by Anderson, 1993). Sympathetic neuroblasts retain the ability to undergo mitosis while expressing differentiated neuronal and catecholaminergic traits (Rothman et al., 1978; Rohrer and Thoenen, 1987). SCG neurons begin to contact their targets in the heart, iris, and salivary glands at E14, when the levels of NGF produced by these tissues increase dramatically (Korsching and Thoenen, 1988). Programmed cell death in the SCG occurs postnatally (Wright et al., 1983).

The present inventors have shown that SCG sympathetic neurons that lack neurofibromin, like NF1 mutant sensory neurons, do not require neurotrophins for prolonged survival in vitro. In the rodent embryo, the survival of sympathetic neurons is first supported by NT3, and the neurotrophin dependence of these neurons subsequently switches to NGF. This switch in dependence is reflected by a switch in receptor expression from TrkC to TrkA (Birren et al., 1993; DiCicco-Bloom et al., 1993; Verdi and Anderson, 1994). However, E13.5 SCG neurons isolated from NF1(−/−) embryos require neither NT3 nor NGF for survival and neurite outgrowth. As for NF1 mutant sensory neurons, cohort studies were performed in low density culture to demonstrate that the loss of neurofibromin has a direct effect on sympathetic neuron survival. Moreover, the survival of NF1 mutant SCG neurons is not affected by an anti-NGF antibody, indicating that autocrine production of NGF is an unlikely mechanism for the neurotrophin-independence of sympathetic neurons that lack neurofibromin. In contrast, SCG neurons isolated from wild-type littermates die within a few days unless NGF or NT3 is added to the culture medium, and fail to survive in the presence of anti-NGF antibody.

The neurotrophin Independence of NF1 Mutant Neurons is Consistent with a Role for Neurofibromin in p21 ras Signalling Pathways.

Neurofibromin shares a region of homology with GTPase activating protein (GAP) and can replace yeast GAP function encoded by the IRA1 and IRA2 genes in complementation assays. GAPs function as negative regulators of p21ras by decreasing the ratio of active GTP-ras to inactive GDP-ras (Bourne et al., 1991; Boguski and McCormick, 1993; Lowy and Willumsen, 1993). In addition, it has been reported that neurofibromin can influence p21ras through a GAP-independent mechanism (Johnson et al., 1994).

Elegant genetic analyses have demonstrated that p21ras is involved in several cell-cell signalling pathways during embryonic development, including the assignment of cell fate to drosophila photoreceptors (Simon et al., 1991; Bonfini et al., 1992) and the induction of vulval structures in C. elegans (Beitel et al., 1990; Han et al., 1990, 1993). p21ras has been implicated in the neurotrophin signalling pathway for embryonic vertebrate neurons. Activated ras protein mimics the survival and neurite-promoting effects of neurotrophins on embryonic chick sensory neurons, and function-blocking antibodies against p21 ras protein abrogate these neurotrophic effects (Borasio et al., 1989; 1993). In addition, neurotrophins increase the proportion of active, GTP-ras in embryonic chick sensory neurons (Ng and Shooter, 1993). The present results are consistent with a model whereby neurofibromin functions as a negative regulator of p21 ras during acquisition of neurotrophin dependence. NF1 mutant neurons survive and acquire mature morphological characteristics in the absence of neurotrophins, just as if the ras signalling pathway were activated constitutively. These data identify NF1 function as epistatic to that of neurotrophins and trk receptors.

Trk Receptor Signalling and Neurofibromin.

Through reverse genetic analysis, the present results identify neurofibromin as a downstream negative regulator of trk receptor signalling in sensory and sympathetic neurons. In the absence of neurotrophins, trk receptors remain inactive and neurotrophin mediated signals are not elicited (Kaplan et al, 1991a,b). It is contemplated that mutational ablation of neurofibromin permits a constitutive, low level signalling to occur which results in neurotrophin-independent survival. Stimulation of the Trk receptors, however, through the addition of neurotrophins would be expected to amplify the low level constitutive signal. This model is consistent with the observed additional stimulation of maturing E13.5 DRG and E12.5 TG mutant neurons by NGF in the mutant cultures. In the likely event that this mechanism occurs via the ras pathway, this model would predict the GTP/GDP ratio of ras protein to be weighted towards the active GTP state due to the loss of NF1 mediated GTPase function. This ratio, however, would be further increased by neurotrophin mediated stimulation of trk receptor and nucleotide exchange activation. In light of recent data suggesting that neurofibromin may modulate ras activity independently of GAP activity (Johnson et al., 1994), this potential function must be included in any model contemplated by the present inventors.

The present results do not rule out an alternative model in which neurofibromin may act as an effector of programmed cell death in embryonic neurons. In this case, neurotrophin/trk signalling would repress NF1 function, while absence of neurotrophin and inactive trk receptors, would permit neurofibromin mediated initiation of programmed cell death. Such a model would not necessarily require an interaction between neurofibromin and p21ras.

The present system depends on the study of ganglionic cultures isolated from individual embryos generated through heterozygous NF1 mutant intercrosses. This places certain constraints that do not readily permit direct testing of the models. One particular strength of using primary cultures is that one can identify and monitor the responses to known environmental cues of individual ganglionic cells including: neuronal precursors, immature neurons, and mature neurons. Thus, one can determine which subpopulation is affected in a given assay. Biochemical approaches would involve mixed ganglionic populations of neurons, neuron precursors, and glia that would only permit detection of net effects that might mask unique conditions in any given subpopulation. In addition, biochemical analyses for ras and other signalling intermediates requires substantially larger numbers of cells than can be obtained from embryonic ganglia cultures. Pharmacological attempts to block p21 ras in NF1 mutant neurons using function-blocking antibodies (Borasio et al., 1993) and benzodiazepine peptidomimetics that inhibit p21ras farnesylation (James et al., 1993, Kohl et al., 1993) may shed light on the mechanisms. Further genetic approaches, including adenovirus-mediated delivery of dominant negative forms of ras pathway molecules to the cultures, will be required to continue validation of the model.

The Tumor Suppressor Gene NF1 has a Role in Neural Development.

Tumor suppressor genes, including NF1, p53, retinoblastoma (RB1), and Wilm's tumor (WT-1), have been the focus of much recent attention for their central roles in human cancer and normal development (reviewed by Knudson, 1993; Weinberg, 1993). Targeted disruption of tumor suppressor genes in mice has allowed detailed analysis of their function during morphogenesis and differentiation. For example, mice homozygous for a defective copy of the RB1 gene die before E16.5 and exhibit abnormalities of the brain, peripheral nervous system, and hematopoietic system (Clarke et al., 1992; Jacks et al., 1992; Lee et al., 1992). Many of the nervous system defects in RB1 null mice appear to be related to the role of retinoblastoma protein in cell cycle control, as excess and ectopic mitotic cells are present in the spinal cord and hindbrain of these embryos (Clarke et al., 1992; Jacks et al., 1992; Lee et al., 1992). The metanephric kidney and gonad fail to develop in mouse embryos homozygous for a defective copy of the WT-1 gene, and these embryos succumb to additional defects in the heart and mesothelium (Kreidberg et al., 1993). Mice that lack functional copies of the p53 gene undergo apparently normal embryonic development and are predisposed to spontaneous neoplasms postnatally (Donehower et al., 1992; Jacks et al., 1994). The present study raises the notion that suppressor oncogenes may have additional roles in the development of neurons which differentiate and mature during embryonic life. Indeed, preliminary studies by the present inventors with p53 null sympathetic neurons indicate that this gene functions in neuronal programmed cell death and proliferation.

A reverse genetic approach has been utilized to demonstrate that neurofibromin has an essential function in the development of neurotrophin dependence in both sensory and sympathetic neurons. Previously, it has been assumed that the etiology of neurofibromas and neurofibrosarcomas in NF1 is a consequence of the altered growth and interactions of Schwann cells. The present results indicate that peripheral neurons are dramatically affected by the loss of neurofibromin function and raise the possibility that this cell type may have a role in the etiology of the disease. A thorough understanding of the regulation of NF1 and other tumor suppressor genes during normal embryogenesis will enhance the development of clinical strategies for treating human neoplasms.

Treatment Modalities

Many attempts including clinical trials, are underway to use neurotrophins as potential therapeutic agents in neurodegenerative, neuromuscular, and trauma induced disorders. While the verdict is still out on the success of such strategies, the methods of the present invention are complementary, synergistic and perhaps more powerful.

The discovery, through the use of the screening methods of the present invention, of any drugs or compounds that render neurofibromin action inactive would be of value, as in cancer chemotherapeutic screens. Similarly, random compounds may be tested in the survival assay. Any compounds that worked would be scrutinized for their mode of action. A variety of standard assays could be used to determine whether the action was at neurofibromin (by inactivation) or elsewhere (i.e., at the receptors) by hyperactivation. These include standard immunoprecipitation with trk specific antibodies followed by western blot probing with anti-phosphotyrosine antibodies to determine the state of receptor activation.

One known enzymatic activity of neurofibromin is GTPase activity. In vitro and in yeast cells, a 325 amino acid subdomain of the neurofibromin peptide can catalyze the dephosphorylation of GTPbound-p21ras (active) to GDPbound-p21ras (inactive). Therefore, any compounds that might specifically inhibit the GTPase activity of neurofibromin, but not of other GTPases, would be valuable candidates to test on neuronal survival and toxicity.

It is understood, therefore, that test tube assays may be used as a preliminary in vitro screening for compounds with a specific effect on the GTPase activity of neurofibromin, but with no effect on other GTPases. The compounds that exhibit this activity may then be used in the more important functional test with live cells as disclosed herein.

It is contemplated that neurofibromin acts as a "dominant-negative" molecule. In light of the present invention, it is contemplated that one may take advantage of this trait by introducing a mutated neurofibromin gene that encodes an inactive or decreased activity enzyme into a normal neuron. This mutant protein would inhibit the action of the normal neurofibromin gene product by interacting with its effector, say ras-GTP, and thus making the effector unavailable for interaction with the normal protein. Mutants with these characteristics can be generated by techniques that are routine and well known in the art, such as random mutagenesis of the NF1 cDNA, for example, followed by a functional test in the survival assay. Introduction of the mutant cDNAs together with appropriate promoters (preferably CMV) into neurons followed by culturing in the absence of neurotrophins will provide the functional assay.

It is contemplated that neurofibromin may exert its negative regulatory function in neurons through the down regulation of p21 ras protein. To design and screen specific mutations in this function, mutagenesis of the relevant (GRD) domain in neurofibromin could be generated, and tested in a yeast two hybrid system with the ras protein. The relevant mutants to screen in the survival assay would be those that can bind the ras protein in the two-hybrid system but are unable to catalyze GTP dephosphorylation. These molecules could then be introduced into neurons to test their biological properties in the survival assay.

Antisense technology

It has now been demonstrated that expression of antisense mRNAs in cells can lead to partial and, in some cases, complete inactivation of a given gene. In the present case, the ultimate goal would be to deliver antisense to neurons specifically. In order to optimize the system, first synthetic antisense oligomers to the NF1 mRNA sequence are prepared. These are introduced into neuronal cultures and tested for their ability to render the neurons independent of neurotrophins. Molecular techniques can be adopted to test for the inactivation of NF1. More advanced goals, that include the inactivation of the NF1 gene in vivo will be less tractable to anti-sense oligomer methods. For this, it will be necessary to express the sequences identified in the previous studies, in anti-sense and under the control of neuron specific promoters. In this way one can aim to specifically inhibit NF1 gene activity in neurons. Among promoters that appear to function exclusively in neurons are the neuron specific enolase (NSE) promoter (Andersen et al., 1992, 1993); the c-fos promoter (Onteniente et al., 1994); HSV-1 LAT promoter (Zwaagstra et al., 1990) and the nestin promoter (Zimmerman et al., 1994).

The preferred method of delivery of antisense or mutant NF1 genes to neurons is the use of adenoviruses as vectors. Adenoviral vectors are preferred because they can be generated at extremely high titers ($10^9$ to $10^{11}$ infectious units per ml). Pilot experiments have produced promising results in that these viral vectors appear to infect neural cells effectively (Le Gall et al., 1993; incorporated herein by reference). In addition, Herpes simplex virus has been demonstrated to be effective in gene delivery to neurons (Breakefield and DeLuca, 1991; incorporated herein by reference). It is understood that any known method of gene delivery including, but not limited to adenovirus, Herpes virus, liposomes or other delivery systems would be encompassed by the present claimed invention.

It is evident that this assay of neuronal survival as performed empirically with NF1 mutant mice, can be extended to a battery of interesting mouse models for neurodegenerative disease. Any strategy that provides promising results in targeting the neurofibromatosis gene product can be applied to cultures from mutant mouse strains that have severe neurological disorders. The issue here may be that permitting constitutive neurotrophin signalling in these mutant cell lines may improve their capacity to survive. Diverse models exist for neurogenic diseases ranging from transgenic models (i.e., neurofilament) to models resulting from spontaneous mutations (i.e, purkinje cell degeneration, spastic, shiverer, etc.).

METHODS

The following methods were used in the preferred practice of the examples that follow.

Cell Culture

Neuron Populations from Mice.

Sensory and sympathetic ganglia were dissected from E11.5-E13.5 mice in Leibowitz L15+ 1×penicillin/streptomycin (Gibco) using watchmaker's forceps and electrolytically sharpened tungsten needles. Embryos were carefully staged according to Theiler and stage-matched embryos were genotyped individually by polymerase chain reaction (Brannan et al., 1994). Embryos that had two copies of the disrupted NF1 allele are referred to as NF1(−/−) or NF1 mutant mice. Studies were performed with littermates and ganglia from different embryos were not pooled. Ganglia were dissociated to single-cell suspensions by gentle trituration with a fire-polished Pasteur pipette after incubation in 0.1% trypsin/calcium and magnesium-free phosphate buffered saline (PBS; Gibco). Trypsin incubation times varied with stage and type of ganglion and ranged from 8 to 20 minutes at 37° C. The action of the trypsin was then inhibited by serum-containing culture medium. Ganglion cells from each embryo were distributed equally among 35 mm tissue culture plastic dishes (Nunc), which had been coated previously with polyornithine (0.5 mg/ml in 0.15M borate buffer; Sigma) and laminin (20 ug/ml in PBS; Gibco). The culture medium consisted of Ham's F14 (Imperial Laboratories) supplemented with 10% heat-inactivated horse serum (JRH Biosciences), 5% heat-inactivated fetal calf serum (Hyclone), 0.5×penicillin/streptomycin (Gibco), and 2 mM glutamine (Gibco). Neurotrophins NGF, BDNF, NT3, and NT4/5 were added to cultures 5 to 6 hours after plating, or at the time of plating. Similar results were obtained when neurotrophins were added to cultures within this time frame. SCG cultures were the exception to this rule; neurons were plated in the absence of neurotrophins and neurotrophins were added at 24 hours, after initial neuron counts had been made. Neurons were counted with the aid of a 5×5 mm grid on an Olympus OMT-2 microscope using phase contrast optics. Cells counted as neurons had phase-bright rounded cell bodies and very thin processes (usually bipolar) that extended at least two times the diameter of the cell body.

Chicken Neurons.

Fertile chicken eggs were incubated at 38° C. in a humidified forced-draft incubator. Embryos were staged according to the Hamburger and Hamilton (1951) criteria. Ganglia and placodes were dissected from embryos in L15 medium (Gibco) using electrolytically sharpened tungsten needles. For the "placode" cultures, entire otic vesicles and third epibranchial placodes (dorsal tip of third bronchial cleft) were dissected out; some neural crest-derived mesenchymal cells were included in the dissection. These tissues were treated with 0.1% trypsin (Worthington) in calcium- and magnesium-free PBS (CMF-PBS; Gibco) at 37° C. for either 9 min (stage 17–20 ganglia), 10 min (stage 21–22 ganglia), or 12 min (placodes). After removal of the trypsin solution, the tissue was washed once in 10 ml of F12(Gibco) medium containing 10% heat-inactivated horse serum and was dissociated into a single-cell suspension in 1 ml of culture medium by gentle trituration using a fire-polished, siliconized Pasteur pipette.

The cells were plated in 8 ml of culture medium in 60 mm plastic tissue culture dishes (Nunc) at a final cell density of 50–150 neurons (stage 19–22 ganglia) or 15–100 neurons (placodes and stage 17–18 ganglia) per dish. To obtain the appropriate density of neurons in placode cultures, 6–8 otic vesicles or third epibranchial placodes were plated per dish. The dishes were previously coated with polyornithine (0.5 mg/ml overnight) and laminin (2 ug/ml for 4 hr) and had a grid (12 mm×12 mm) scored on their undersurface. The culture medium was F14 (Gibco) supplemented with penicillin (60 mg/l), streptomycin (100 mg/l), glutamine (100 mM), 10% heat-inactivated horse serum (Gibco), and 5% heat-inactivated fetal calf serum (Gibco). The cultures were maintained in a humidified $CO_2$ (3.5%) incubator at 37.5° C. Twelve hours (ganglia) or 24 hr (placodes) after plating, the positions of the neurons within the grid were recorded, this being the initial cohort of neurons whose survival was monitored throughout the culture period. Neurons that arose in otic vesicle cultures resembled vestibular neurons (short neurites), and those that arose in third epibranchial placode cultures resembled nodose neurons (long neurites). Some placode cultures were stained with an antiserum that recognizes the avian 68 kd neurofilament subunit (Davies, 1989) to show that cells that were counted, neurons expressed a neuron-specific marker. It has recently been demonstrated by the inventors that the neurons in early ganglion cultures arise from placodal ectoderm and not from neural crest.

DRGs were dissected from the thoracic and lumbosacral regions of E4.5 (stages 25/26; Hamburger and Hamilton, 1951) chicken embryos. Following trypsinization (0.1% trypsin in Ca2+- and Mg2+- free phosphate-buffered saline [PBS] for 12 min at 37.5° C., the ganglia were washed with F12 medium (GIBCO) plus 10% heat-inactivated horse serum and were gently triturated in culture medium (F14 medium, 10% heat-inactivated horse serum, 5% heat-inactivated fetal calf serum) using a siliconized, fire-polished Pasteur pipette. The resulting single-cell suspension was mixed with additional culture medium such that each well of 35 mm, 4 well plastic tissue culture dishes (Sterilin) received 50 ul of medium continuing 200–400 cells. The wells were precoated with polyornithine (0.5 mg/ml, overnight) and laminin (20 ul/ml for 4 hr) and had 4×4 mm grids scored on the base for cell counting. The 35 mm dishes were placed in a large petri dish containing moist tissue paper to prevent evaporation of the small volume of medium in the wells. After a 1.5 hr incubation at 37.5° C. in a humidified 3.5% $CO_2$ incubator, the serum-containing medium was removed and replaced with defined medium (F14 plus 2 mM glutamine, 0.35% bovine serum albumin, 60 ng/ml progesterone, 15 ug/ml putrescine, 400 ng/ml L-thyroxine, 38 ng/ml sodium selenite, and 340 ng/ml tri-iodo-thyronine). As appropriate, neurotrophic factors and/or oligonucleotides were added to the culture medium at this time.

BDNF was purified from adult pig brains by the methods of Barde et al. (1993) with modifications Kalcheim et.al., 1987). BDNF was added to cultures at a concentration of 5 ng/ml; lower concentrations of BDNF were less effective at promoting neuron survival. For cultures exposed to BDNF for brief periods, BDNF was removed by washing cultures twice with F12 plus 10% heat-inactivated horse serum (2 min per wash) and once with culture medium (20 min at 37.5° C.), prior to adding 8 ml of fresh culture medium. Control cultures (no BDNF) and cultures that received BDNF throughout in the same experiment were washed at the same time and in the same manner. NGF was purified from adult male mouse submandibular salivary glands by the method of Bocchini and Angeletti (1969). NGF was added to some cultures at a concentration of 2 ng/ml.

Neuron Cohorts.

The following section describes neuron cohorts as practiced using mouse neurons, however, this technique is routinely adapted to chicken neurons. Sensory and sympathetic ganglia were dissected and dissociated as above, and cell suspensions were plated at very low density (50–200 cells/dish) on 60 mm tissue culture plastic dishes (Falcon) that had 5×5 mm grids scored on the bottoms. After 6–24 hours, cohorts of neurons were identified and drawn on graph paper; the survival of these neurons was monitored every 24 hours for a period of 4–5 days. Dead neurons remained as "carcasses" for 24–48 hours (Vogel and Davies, 1991). Neurotrophins were added to the culture medium after neuron cohorts were identified.

Isolated Neurons.

E12.5 DRG from stage-matched NF1(−/−) and wild-type littermates were dissected and dissociated to single-cell suspensions as described above. The cell suspensions were diluted in culture medium to a concentration of approximately one cell per 10 ul. Ten ul of diluted cell suspension were added to 200 ul of culture medium in each well of a 96-well plate (Corning) that had been coated previously with polyornithine and laminin. After 18 hours, wells were examined for the presence of lone neurons; wells that contained single neurons were marked and neuron survival was monitored each day for a period of 4 days. Neurotrophins NGF, BDNF, and NT3 were added to some of the wells containing wild-type neurons.

Conditioned Medium.

E12.5 DRG or E13.5 SCG from NF1(−/−) and wild-type littermates were dissected and dissociated to single-cell suspensions as described above. The NF1 mutant cell suspensions were plated at very high density (0.5–2 ganglia per well) in 500 ul of culture medium in the wells of a 24-well plate (Nunc) that had been coated previously with polyornithine and laminin. Neurotrophins (NGF, BDNF, NT3, 2 ng/ml each) were added to wells containing NF1 mutant neurons. After 24, 72, or 120 hours, wild-type cultures were washed three times with culture medium and the media conditioned by NF1 mutant ganglion cells were added to the wild-type cells. The NF1 mutant cells received 500 ul of fresh culture medium. Neuron survival was monitored in NF1 mutant and wild-type cultures for several days following the medium "switch".

Cell Proliferation.

E12.5 DRG from stage-matched NF1(−/−) and wild-type littermates were dissected and dissociated to single-cell suspensions as above. The cells were resuspended in culture medium containing a 1:1000 dilution of 5-bromo-2'-deoxyuridine labelling reagent (BRDU; Amersham) and neurotrophins NGF, BDNF, and NT3 (2 ng/ml each). The cell suspensions were plated in 35 mm tissue culture plastic dishes (Nunc) that had been coated previously with polyornithine and laminin. After 24 hours, the cells were fixed for 1 hour in 4% paraformaldehyde (Fluka) in L15 and permeabilized 30 minutes in 0.05% Triton X100+5% HIHs in PBS at room temperature. The cultures were immunostained with anti-BRDU according to manufacturer's instructions (Amersham RPN 20 Cell Proliferation Kit).

Anti-NGF Treatment.

E13.5 SCG from stage-matched NF1(−/−) and wild-type littermates were dissected and dissociated to single-cell suspensions as above. Cell suspensions were distributed equally in culture medium among 35 mm tissue culture plastic dishes (Nunc) that had been previously coated with polyornithine and laminin. After 24 hours, the neurons in each dish were counted, and NGF (1 ng/ml) and/or anti-NGF (monoclonal 27/21, 10–20 ng/ml; Boehringer) were added to the culture medium. Neurons were counted again at 72 and 96 hours.

Retrograde Labelling

E13.5 NF1(−/−) and wild-type embryos were decapitated and the heads were fixed in 4% paraformaldehyde/PBS overnight at 4° C. DiI (1,1'-dioctadecyl-3,3,3',3'-tetramethylindocarbacyanine perchlorate; Molecular Probes) crystals were inserted into the epithelium and mesenchyme of the maxillary process. The labelled heads were placed in 10% formalin and incubated at 37° C. After one week, the heads were embedded in agar/sucrose and sectioned at 120 um on a vibratome. DiI-labelled trigeminal neurons were visualized on an Olympus microscope using a rhodamine filter set.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Sensory Neurons

Dorsal Root Ganglion.

During normal murine development, the majority of DRG neurons become dependent on NGF for survival between E12.5 and E13.5, after the proliferation of neuronal precursors has ceased (Lawson and Biscoe, 1979). To determine whether sensory neurons that lack neurofibromin exhibit altered responsiveness to NGF, dissociated cultures of DRG from individual E13.5 NF1 (−/−) and wild-type embryos were established in the presence and absence of NGF. NGF was added to wild-type cultures 5 to 6 hours after plating; identical results were obtained if NGF was added at the time of plating. As indicated in FIG. 1 and FIG. 2A–FIG. 2D, many E13.5 DRG neurons isolated from NF1 mutant embryos extend neurites and survive for 48 hours and longer in the absence of NGF. In contrast, very few E13.5 DRG neurons isolated from wild-type littermates survive 48 hours in the absence of NGF (FIG. 1). As anticipated, in the presence of NGF, wild-type DRG neurons extend elaborate neurite arbors and survive for several days in culture (FIG. 2A–FIG. 2D).

Figure 3A:
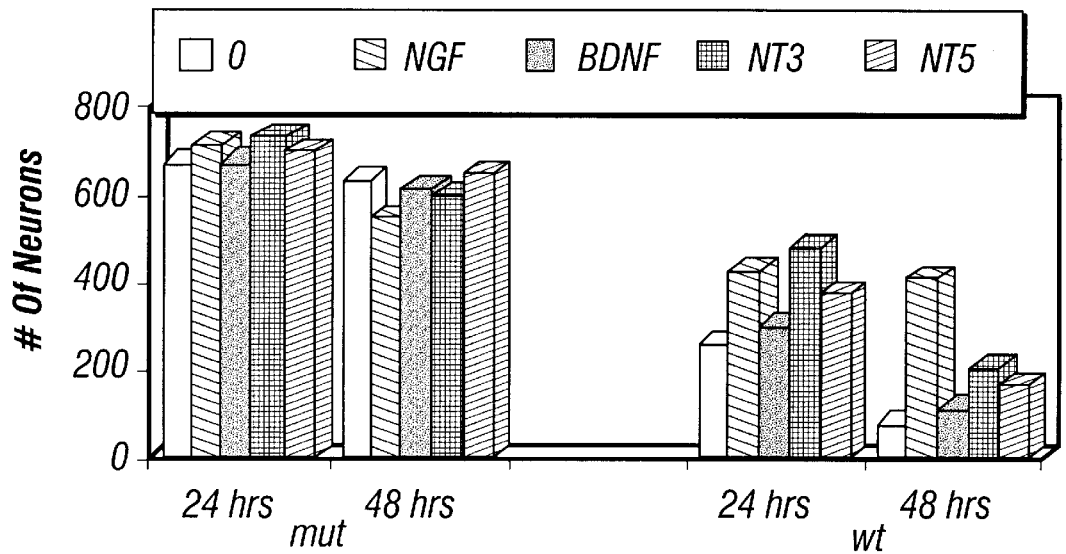
FIG. 3A. NF1 mutant DRG (E12.0) and trigeminal neurons (E11.5) neurons fail to become responsive to neurotrophins in vitro. Ten replicate cultures were established from stage-matched mutant and wild-type embryo DRGs; each bar represents the average of values from 2 cultures. Neurotrophins NGF, BDNF, NT3, and NT5 were added 5–6 hours after plating at a concentration of 2 ng/ml each. Similar results were obtained with E12 DRG neurons isolated from mutant and wild-type embryos from one additional litter.

Both avian and mammalian sensory neurons exhibit a period of neurotrophin-independent survival prior to the onset of target innervation (Davies and Lumsden, 1984; Vogel and Davies, 1991). Sensory neurons isolated from young embryos prior to, or during, early phases of target innervation acquire neurotrophin dependence with timing that parallels the temporal development of neurotrophin dependence acquisition in vivo (Vogel and Davies, 1991). To determine whether sensory neurons that lack neurofibromin could acquire neurotrophin dependence in vitro, DRG neurons were isolated from NF1 mutant and wild-type embryos at the onset of the period of target innervation. For cultures of these younger neurons, neurotrophins were added 6 to 12 hours after plating. Unlike normal neurons, E12.0 DRG neurons isolated from NF1(−/−) embryos do not become dependent on NGF for survival over time in culture (FIG. 3A). Even after prolonged culture periods, NF1 mutant DRG neurons isolated prior to target innervation do not respond to neurotrophins in vitro (Table 1A). Many wild-type E12.0 DRG neurons survive 24 hours in the absence of neurotrophins; however, by 48 hours in vitro the majority of DRG neurons are dependent on NGF for survival (FIG. 3A, Table 1A).

NF1 Mutant DRG Neurons Exhibit Enhanced Survival.

Sensory ganglia isolated from young embryos contain neuronal precursors that proliferate and differentiate in vitro (Ernsberger and Rohrer, 1987). To determine whether neuronal precursor proliferation is enhanced by the loss of neurofibromin, cultures of NF1 mutant and wild-type E12.5 DRG were labeled with bromodeoxyuridine for 24 hours. In two independent studies, no difference was observed in the proportion of BRDU-labelled neurons between NF1 mutant and wild-type cultures. Indeed, very few (<1%) neurons were BRDU-labelled in both NF1 mutant and wild-type cultures.

To establish further that the increased numbers of neurons observed in cultures of NF1 mutant ganglia arose through enhanced neuron survival rather than differentiation of precursors, the survival of individual identified neurons was monitored over a period of several days. Table 2 shows that over 60%; of E12.5 NF1 mutant DRG neurons identified at 24 hours in vitro survive for four additional days in the absence of neurotrophins. Although some mature (E13.5) NF1 mutant DRG neurons respond to NGF, addition of neurotrophins to the culture medium has no effect on the survival of younger E12.5 DRG neurons isolated from NF1(−/−) mice (Table 2). Very few of the normal E12.5 DRG neurons isolated from wild-type littermates survive for two additional days unless neurotrophins are added to the culture medium (Table 2). Moreover, single E12.5 NF1 mutant DRG neurons isolated in individual tissue culture wells survive for four days in the absence of neurotrophins (11/13 single neuron cultures), whereas none of the single neurons from wild-type littermates survived to 48 hours unless neurotrophins were added to the culture medium.

These cohort and single cell studies demonstrate that DRG neurons isolated from NF1(−/−) embryos have altered survival requirements for neurotrophins when compared to wild-type neurons. Specifically, a large proportion of NF1 mutant neurons survive and extend neurites in the absence of NGF. However, it remained possible that NF1(−/−) neurons produce and respond to endogenous neurotrophins in vitro, through an autocrine effect. To determine if NF1 mutant DRG neurons and glia produced trophic factors in vitro, E12.5 NF1(−/−) DRG cells were allowed to condition media for 24 or 72 hours and these media were used to attempt to promote the survival of wild-type E12.5 DRG neurons. Media conditioned by NF1 mutant DRG cells failed to support the survival of wild-type neurons in the absence of neurotrophins (0/8 wells), indicating that mutant neurons and glia do not produce detectable amounts of survival-promoting factors. Taken together, these data indicate that functional disruption of the NF1 gene results in neurotrophin-independent DRG sensory neuron survival.

Trigeminal Ganglion.

Figure 4:
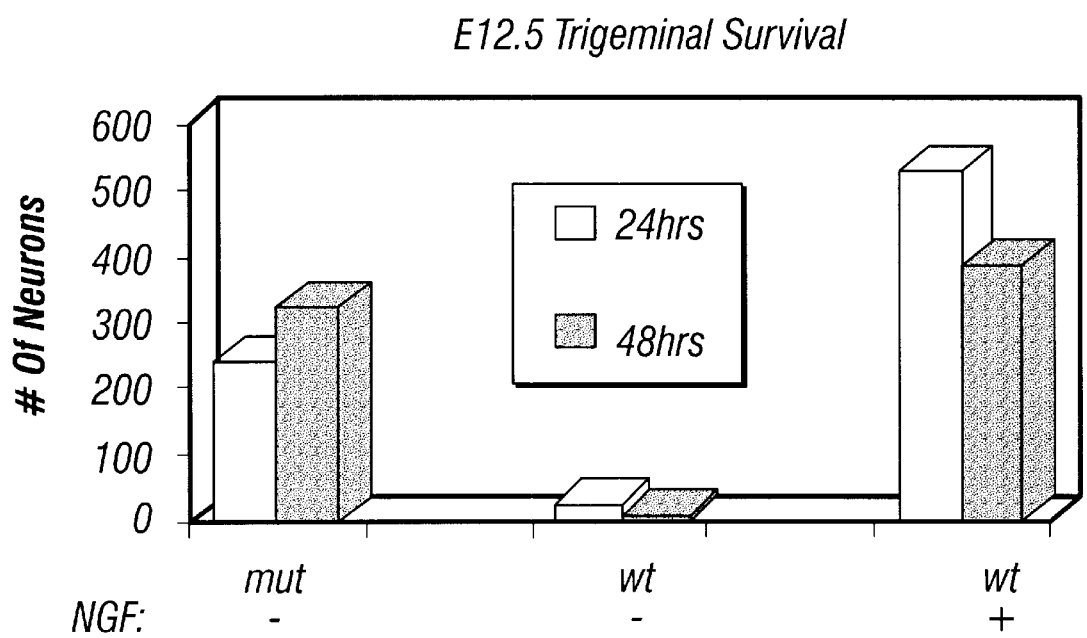
FIG. 4. NF1 mutant E12.5 trigeminal neurons survive in the absence of NGF. Replicate cultures were established from stage-matched NF1 mutant and wild-type embryos; NGF was added to wild-type cultures at a concentration of 1 ng/ml. Similar results were obtained with ganglia taken from mutant and wild-type embryos from 2 additional litters. For NF1 mutant cultures, the range of values at 24 hours is 214–300 neurons and at 48 hours 276–391 neurons. For wild-type cultures in the presence of NGF, the range of values at 24 hours is 510–555 neurons and at 48 hours 381–403 neurons.

In the mouse, embryonic trigeminal neurons become dependent on NGF for survival between E11.5 and E12.5 (Buchman and Davies, 1993). Trigeminal neurons isolated prior to this period survive and extend neurites in the absence of neurotrophins, but acquire NGF dependence with time in vitro (Davies and Lumsden, 1984). Acquisition of NGF dependence in vivo coincides with the arrival of trigeminal axons at their peripheral targets and with production of NGF by target maxillary process epithelium (Davies at al., 1987). To determine whether trigeminal neurons that lack neurofibromin require NGF for survival, dissociated cultures were established of trigeminal ganglia from E12.5 NF1(−/−) and wild-type mice in the presence and absence of NGF. Like NF1 mutant DRG neurons, trigeminal neurons isolated from NF1(−/−) embryos extend neurites and survive for several days in the absence of NGF (FIG. 4). In contrast, few wild-type E12.5 trigeminal neurons survive 48 hours in the absence of NGF; wild-type neurons extend elaborate neurite arbors and survive for several days only when NGF is added to the culture medium (FIG. 4).

Figure 3B:
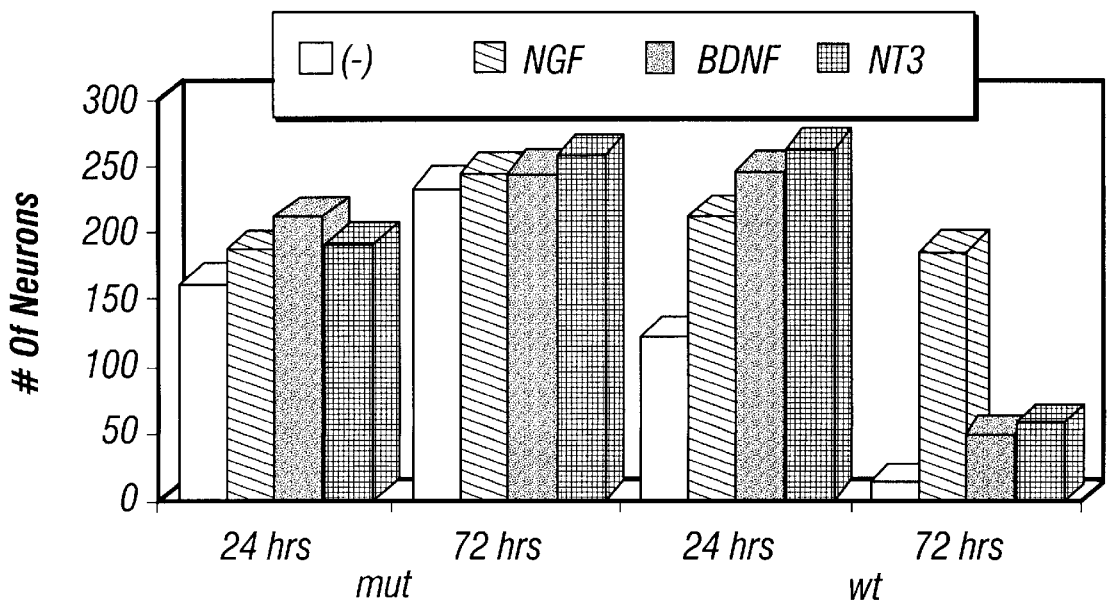
FIG. 3B. Four replicate trigeminal neuron cultures were established from stage-matched mutant and wild-type embryos; neurotrophins NGF, BDNF, and NT3 were added at 2 ng/ml each. Similar results were obtained with E11.5 TG neurons isolated from 2 additional mutant and wild-type pairs.

To determine whether trigeminal neurons that lack neurofibromin can acquire NGF dependence in vitro, dissociated cultures were established of E11.5 trigeminal ganglia from NF1(−/−) and wild-type embryos in the presence and absence of neurotrophins. Although many wild-type E11.5 trigeminal neurons survive for 24 hours in the absence of neurotrophins, by 48 hours in vitro the majority of these neurons have acquired dependence on NGF for survival (FIG. 3B, Table 1B). E11.5 trigeminal neurons isolated from NF1 mutant embryos become dependent on NGF for survival (FIG. 3B). Even after prolonged culture periods, NF1 mutant trigeminal neurons isolated prior to target innervation fail to acquire neurotrophin dependence in vitro (Table 1B).

NF1 Mutant Neurons Develop Appropriate Axonal Target Contacts.

Figure 5A:
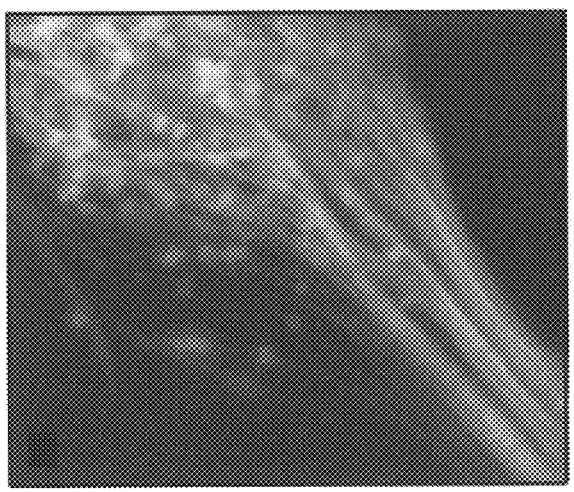
FIG. 5A. NF1 mutant trigeminal neurons contact the maxillary process. Wild type trigeminal neurons retrogradely labelled with diI, E13.0 embryo. Maxillary branch of trigeminal nerve extends toward lower left.
Figure 5B:
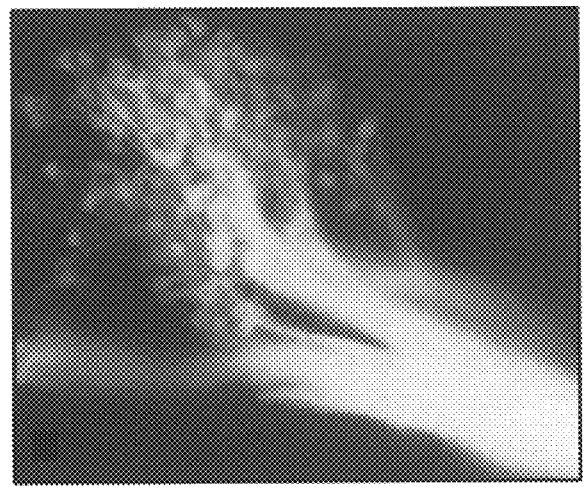
FIG. 5B. Mutant trigeminal neurons retrogradely labelled with diI, E13.0 NF1(−/−) embryo.

A possible explanation for the observed neurotrophin independence of NF1 mutant neurons could relate to retarded embryonic development resulting in a failure to contact appropriate peripheral targets with the same timing as their wild type counterparts. To determine whether trigeminal neurons in NF1(−/−) embryos extended axons to the usual peripheral targets, an attempt was made to label trigeminal neurons retrogradely with DiI from the maxillary process in E13.0 NF1 mutant and wild-type embryos. Application of this dye at the peripheral target results in labelling of cell bodies at the ganglion only if axons have successfully reached their targets. Numerous trigeminal neurons were labeled, and the patterns of trigeminal axon fasciculation and trajectories to the maxillary process appeared similar in NF1 mutant (5/5) and wild-type (4/4) embryos (FIG. 5A–FIG. 5B). In addition, the DiI-labeled central axons of trigeminal neurons were observed in the hindbrains of both NF1(−/−) and wild-type embryos. Thus, although trigeminal neurons that lack neurofibromin exhibit altered patterns of neurotrophin dependence, the initial stages of central and peripheral target innervation appear to occur normally and with correct timing in mutant embryos.

Nodose Ganglion.

Figure 6:
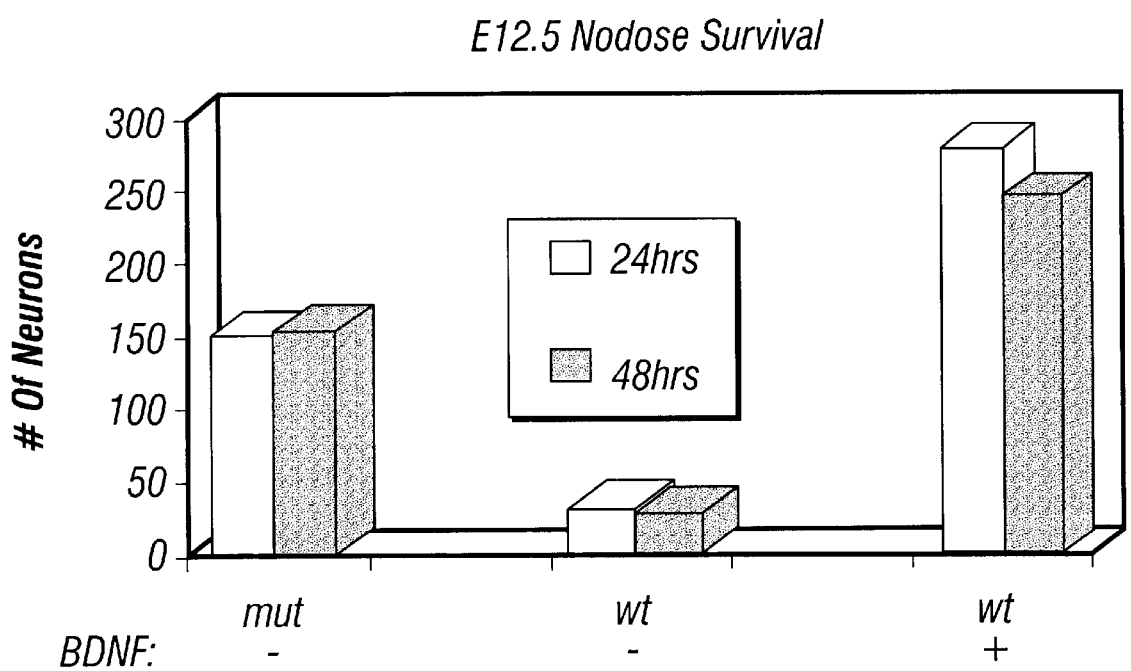
FIG. 6. NF1 mutant E12.5 nodose neurons survive in the absence of BDNF. Replicate cultures were established from stage-matched mutant and wild-type embryos; BDNF was added to wild-type cultures at a concentration of 2 ng/ml. Similar results were obtained with NG taken from mutant and wild-type embryos from 3 additional litters. For the NF1 mutant cultures, the range of values at 24 hours is 146–152 neurons and at 48 hours 146–156 neurons. For the wild-type cultures in the presence of BDNF, the range of values is 230–326 neurons and at 48 hours 199–285 neurons.

The nodose ganglion forms adjacent to the superior cervical ganglion and its neurons arise from placodal ectoderm rather than from the neural crest (D'Amico-Martel and Noden, 1983). In culture, nodose ganglion neurons isolated from wild-type E12.5 mouse embryos depend on exogenous BDNF to survive and extend neurites (FIG. 6; Davies et al., 1994). The present studies indicate that these placode-derived neurons that lack neurofibromin also lose requirement for neurotrophins. Thus, in contrast to wild type neurons, dissociated nodose neurons isolated from NF1 mutant embryos extend neurites and survive for 48 hours in the absence of added neurotrophins (FIG. 6). To document that absence of neurofibromin function has a direct effect on survival, cohorts of E13.0 nodose neurons were identified in very low density cultures and their appearance was monitored over a period of 5 days. More than 50% of NF1 mutant nodose neurons identified at 24 hours in vitro were found to survive an additional 4 days in the absence of neurotrophins. In contrast, all wild-type nodose neurons identified at 6 hours in vitro die by 48 hours unless BDNF is added to the culture medium. Thus, functional disruption of the NF1 gene has a direct effect on the survival of sensory neurons that are normally BDNF-dependent and do not arise from the neural crest.

NF1 Mutant Sensory Neurons can Respond to Neurotrophins.

Figure 7A:
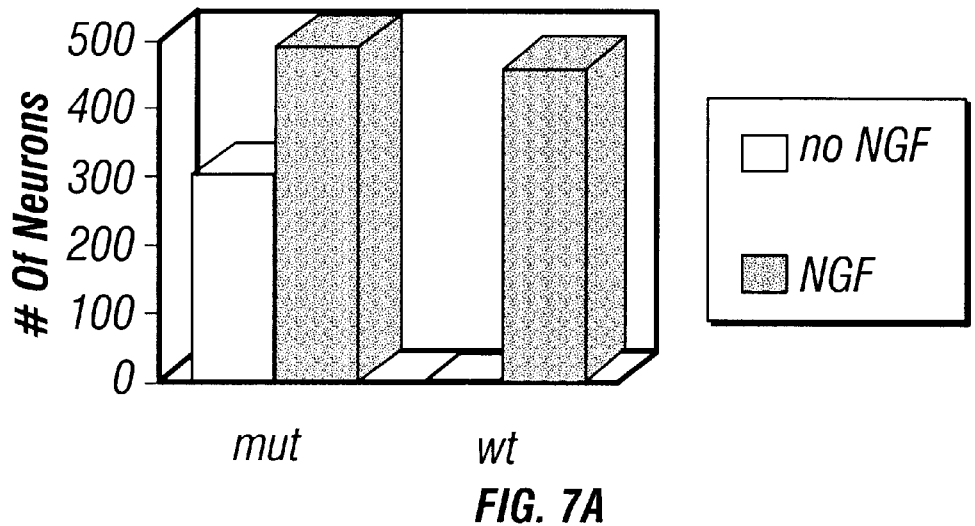
FIG. 7A. A subpopulation of NF1 mutant sensory neurons respond to NGF with enhanced survival and are tenfold more sensitive to the survival-promoting effects of NGF. Ten replicate E13.5 DRG cultures were established from each embryo. For the NF1 mutant embryo, 5 cultures were treated with NGF at 500 pg/ml and 5 cultures received no neurotrophins. For the wild-type littermate, 8 cultures were treated with NGF and 2 received no neurotrophins. The range of values for NF1 mutant cultures in the absence of NGF is 275–316 neurons; in the presence of NGF, the range is 464–518 neurons. The range of values for wild-type cultures in the presence of NGF is 417–511 neurons.

Addition of neurotrophins to immature cultures of sensory neurons had no detectable effects on their subsequent survival in the presence or absence of neurotrophins (FIG. 3A, FIG. 3B, Table 1). However, cultures of sensory neurons isolated during the period of maturation and target innervation did exhibit a partial response to NGF. FIG. 7A shows that added NGF increases the number of neurons that survive 24 hours in cultures of both NF1 mutant and wild-type E13.5 DRG. Moreover, these NGF-dependent NF1(−/−) DRG neurons are approximately tenfold more sensitive to the survival-promoting effects of NGF than their wild-type (+/+ or +/−) counterparts (20 pg/ml vs. 200 pg/ml).

Figure 7B:
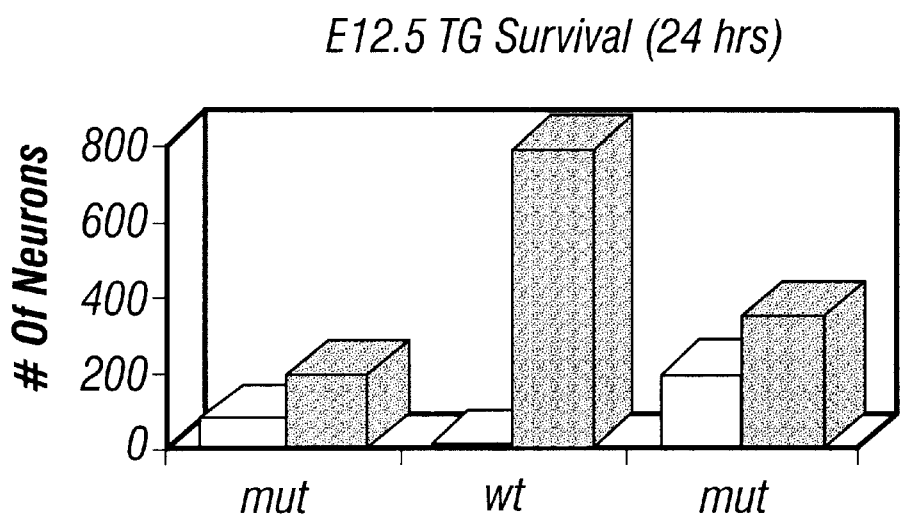
FIG. 7B. Four replicate E12.5 trigeminal cultures were established from each of 2 NF1 mutant embryos and one wild-type embryo. For each embryo, 2 dishes were treated with NGF (500 pg/ml) and 2 dishes received no neurotrophins. Similar results were obtained with E12.5 TG neurons isolated from mutant and wild-type embryos from 2 additional litters. Trigeminal ganglia dissected from NF1 mutant embryos are often smaller than wild-type TG and contain fewer neurons.

Similarly, in most studies, mature trigeminal neurons isolated from NF1(−/−) embryos are NGF-independent. However, at E12.5, an additional population of NF1 mutant trigeminal neurons can be maintained in cultures with added NGF. FIG. 7B shows that at this stage, NGF increases the number of neurons that survive to 24 hours in cultures of both NF1 mutant and wild-type trigeminal ganglia. As seen with NF1 mutant DRG neurons, these NGF-dependent trigeminal neurons isolated from NF1(−/−) embryos after target contact are approximately tenfold more sensitive to the survival-promoting effects of NGF than those isolated from wild-type (+/−) littermates (maximum survival response at 20 pg/ml vs. 200 pg/ml).

EXAMPLE 2

Sympathetic Neurons

Superior Cervical Ganglion.

The maturation of sympathetic neurons occurs later in development than that of sensory neurons. The majority of wild-type SCG neurons are dependent on NGF for survival by E16.5 (Coughlin and Collins, 1985). Prior to E16, wild-type SCG contain many immature neurons that are undergoing proliferation (DiCicco-Bloom et al., 1990). In addition, the period of neuron death in the SCG occurs postnatally rather than during embryogenesis (Wright et al., 1983). Since NF1(−/−) embryos die by E13.5, examination was restricted to neurotrophin dependence in SCG neurons prior to the period of target innervation (Rubin, 1985). After 48 hours in culture, wild-type E13.5 SCG neurons begin to die in the absence of neurotrophins, and a subpopulation of neurons are supported by NGF at this stage (FIG. 8A, FIG. 9A–FIG. 9D). To examine whether sympathetic neurons that lack neurofibromin acquire NGF-dependence in vitro, dissociated cultures were established of E13.5 SCG isolated from NF1(−/−) and wild-type embryos. As observed for peripheral sensory neurons, NF1 mutant sympathetic (SCG) neurons extend neurites and survive in the absence of NGF; none of the neurotrophins tested had any effect on the survival of NF1 mutant SCG neurons (FIG. 8A, FIG. 9A–FIG. 9D). SCG mutant neurons have been maintained in culture for periods of three weeks in the absence of neurotrophins with no detectable effects from addition of NGF (FIG. 8B, FIG. 9A–FIG. 9D).

Figure 8A:
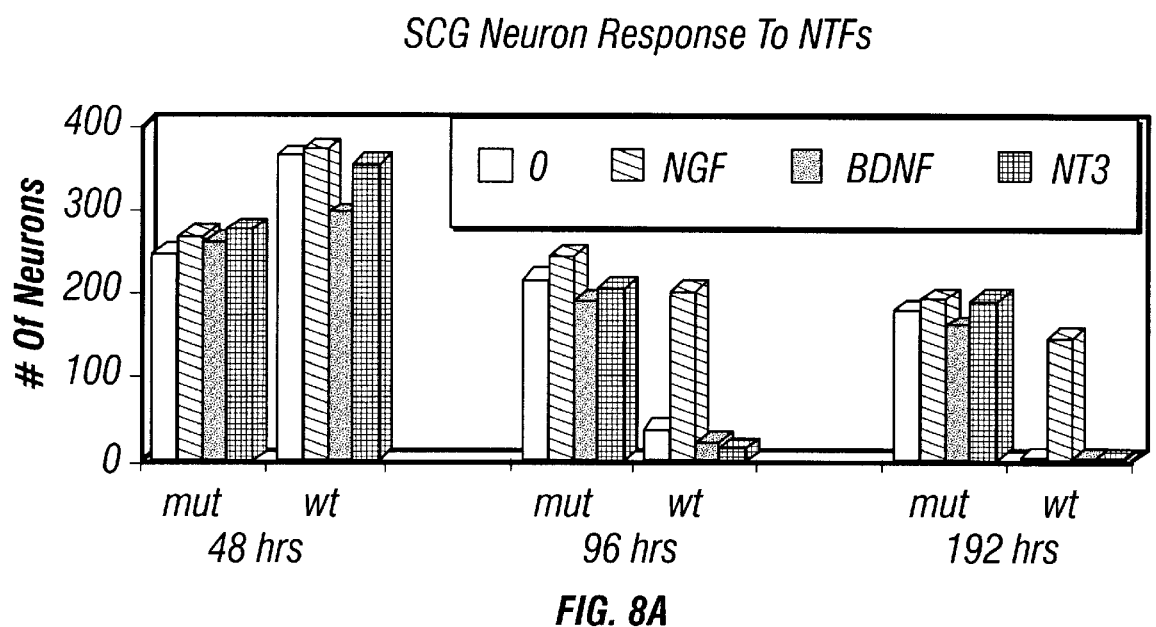
FIG. 8A. NF1 mutant E13.5 SCG neurons fail to become responsive to neurotrophins in vitro and survive in the absence of NGF. Eight replicate cultures were established from stage-matched mutant and wild-type embryos; each bar represents the average of values from 2 cultures. Neurotrophins NGF, BDNF, and NT3 were added at 2 ng/ml each. Similar data were obtained with SCG neurons isolated from mutant and wild-type embryos from 2 additional litters.
Figure 8B:
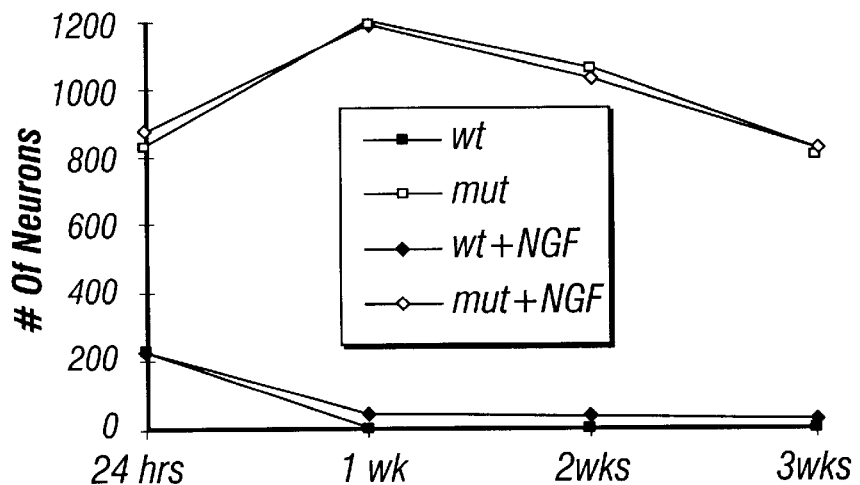
FIG. 8B. Six replicate cultures were established from stage-matched mutant and wild-type embryos; for each embryo, 3 cultures were treated with NGF at 1 ng/ml and 3 cultures received no neurotrophins. For the NF1 mutant embryo, the ranges of values for no NGF were 1111–1304 neurons at one week, 903–1123 neurons at 2 weeks, and 742–938 neurons at 3 weeks. In the presence of NGF, the ranges were 1084–1298 neurons at one week, 890–1099 neurons at 2 weeks, and 694–892 neurons at 3 weeks.
Figure 8C:
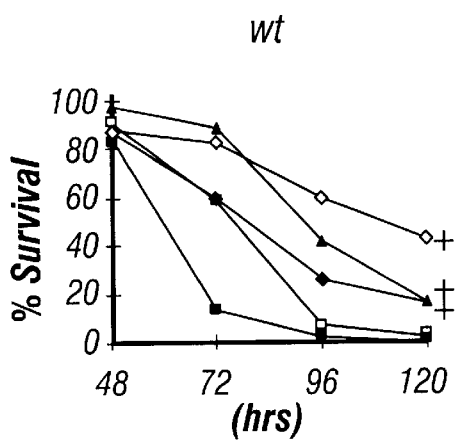
FIG. 8C. For each embryo, 5 replicate cultures were established at very low cell density. Neuron cohorts were identified at 24 hours; for the NF1 mutant embryo, NGF (1 gn/ml) was added to 2 cultures.
Figure 8D:
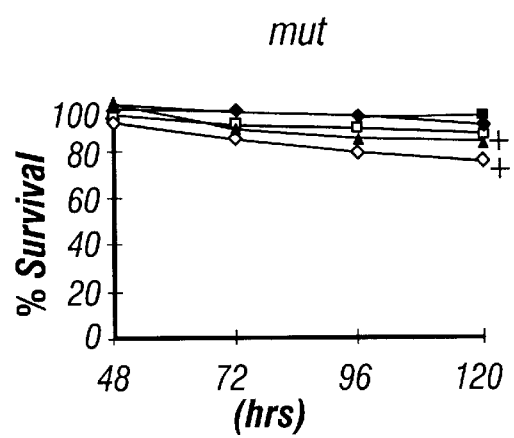
FIG. 8D For the wild-type embryo NGF was added to 3 cultures as in FIG. 8C. Neuron cohorts were monitored each day for 4 additional days.

Previous studies demonstrated that both the SCG and paravertebral sympathetic ganglia in NF1(−/−) embryos contain excess neurons at the time of death (Brannan et al., 1994). To determine whether the increase in SCG neuron numbers observed in NF1 mutant cultures was due to enhanced proliferation or increased neuron survival, the survival of individual identified E13.5 SCG neurons isolated from NF1(−/−) and wild-type mice was monitored. FIG. 8C shows that over 90% of the NF1 mutant SCG neurons identified at 24 hours survive four additional days in the absence of neurotrophins. In contrast, less than 3% of the wild-type SCG neurons identified at 24 hours survive four additional days in the absence of NGF (FIG. 8C). Thus, although NF1 may have a role in proliferation of sympathetic neuronal precursors in embryos, the loss of neurofibromin results in the neurotrophin-independent survival of E13.5 SCG neurons.

To determine whether NF1 mutant SCG neurons and glia produce survival factors in vitro, E13.5 NF1(−/−) SCG cells were allowed to condition media for 72 or 120 hours and these media were used to attempt to promote the survival of wild-type E13.5 SCG neurons. Media conditioned by NF1 mutant SCG cells failed to support the survival of wild-type neurons in the absence of neurotrophins (0/6 wells), indicating that mutant neurons and glia do not produce detectable amounts of survival-promoting factors in this assay.

Figure 10:
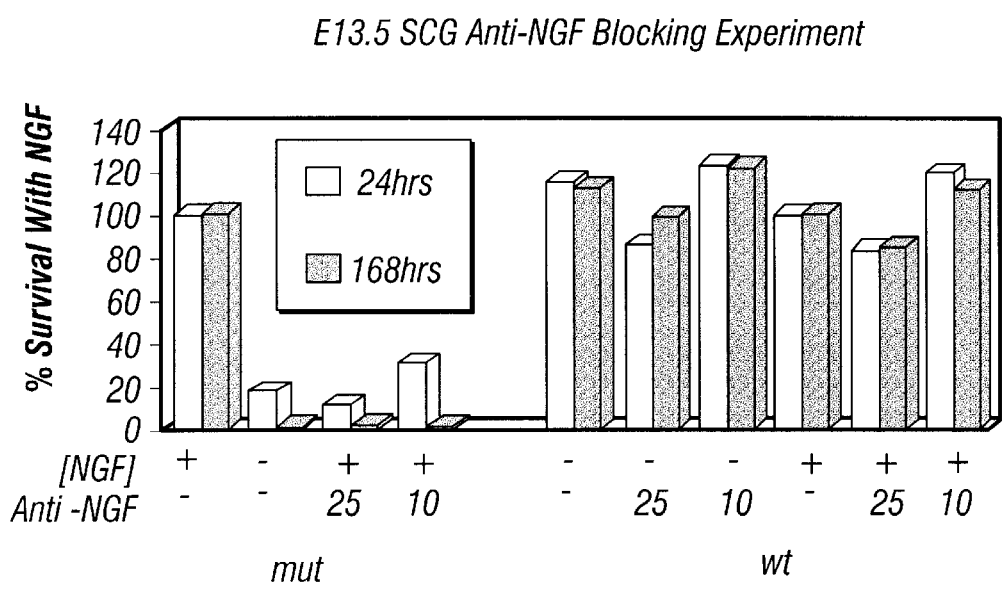
FIG. 10. NGF blocking antibody does not affect the survival of NF1 mutant SCG neurons. Twelve (NF1 mutant) and eight (wild-type) replicate cultures were established from stage-matched embryos; each bar represents the average of values from two cultures. NGF was added at 1 ng/ml and anti NGF antibody at either 25 ng/ml or 10 ng/ml. Similar results were obtained in 3 additional studies.

Since NF1 mutant sensory neurons are at least tenfold more sensitive to NGF in dose-response analyses, it remained formally possible that NF1 mutant neurons could produce and respond to minute amounts of NGF that are suboptimal to support the survival of wild-type neurons. An attempt was made therefore, to perturb the survival of NF1 mutant SCG neurons with an antibody that blocks the effects of NGF (Rohrer et al., 1988). Wild-type E13.5 SCG neurons die when anti-NGF antibody is added to their culture medium (FIG. 10). In contrast, anti-NGF antibody, at levels that block the action of 1 ng/ml NGF, has no effect on the survival or morphology of NF1 mutant SCG neurons (FIG. 10). Taken together, the results of the conditioned medium and NGF-blocking experiments indicate that NF1(−/−) SCG neuron survival and neurite outgrowth are not promoted by autocrine NGF production.

Table 1A.

NF1 mutant E12.0 DRG neurons fail to acquire neurotrophin dependence after a prolonged culture period. Four replicate cultures of DRG neurons were established from stage-matched NF1 mutant and wild-type embryos. Neurotrophins were added to the culture medium 12 hours after plating at a concentration of 2 ng/ml. The increases in neuron number in both wild-type and NF1 mutant cultures result from differentiation and maturation of neuron precursors and young neurons.

TABLE 1A

| | | Number of E12.0 DRG Neurons | | | | |
|---|---|---|---|---|---|---|
| Embryo | Genotype | NTFs | 24 hrs | 48 hrs | 72 hrs | 96 hrs |
| DRG1 | wt | (−) | 180 | 82 | 30 | 6 |
| | NF1(+/−) | NGF | 680 | 896 | 845 | 641 |
| | | BDNF | 316 | 337 | 225 | 127 |
| | | NT3 | 397 | 333 | 194 | 57 |
| DRG2 | mut | (−) | 147 | 282 | 273 | 276 |
| | NF1(−/−) | NGF | 172 | 280 | 199 | 182 |
| | | BDNF | 169 | 221 | 203 | 169 |
| | | NT3 | 235 | 332 | 325 | 288 |

Table 1B.

NF1 mutant E11.5 trigeminal neurons fail to acquire neurotrophin dependence after a prolonged culture period. Four replicate cultures of trigeminal neurons were established from stage-matched NF1 mutant and wild-type embryos. Neurotrophins were added to the culture medium 12 hours after plating at a concentration of 2 ng/ml.

TABLE 1B

| | | Number of E11.5 Trigeminal Neurons | | | | |
|---|---|---|---|---|---|---|
| Embryo | Genotype | NTFs | 24 hrs | 48 hrs | 72 hrs | 96 hrs | 120 hrs |
| TG1 | wt | (−) | 123 | 91 | 14 | ND | ND |
| | NF1(+/−) | NGF | 213 | 337 | 186 | ND | ND |
| | | BDNF | 145 | 203 | 48 | ND | ND |
| | | NT3 | 263 | 228 | 59 | ND | ND |
| TG2 | mut | (−) | 163 | 233 | 235 | 234 | 225 |
| | NF1(−/−) | NGF | 189 | 282 | 244 | 254 | 252 |
| | | BDNF | 212 | 246 | 245 | 243 | 241 |
| | | NT3 | 197 | 260 | 261 | 246 | 253 |
| TG3 | mut | (−) | 52 | 74 | 68 | 61 | 64 |
| | NF1(−/−) | NGF | 59 | 52 | 57 | 48 | 42 |
| | | BDNF | 66 | 83 | 82 | 80 | 84 |
| | | NT3 | 70 | 92 | 98 | 77 | 80 |

Table 2. Loss of neurofibromin results in the neurotrophin-independent survival of E12.5 DRG neurons in low-density culture. Very low density cultures of DRG were established from stage-matched NF1 mutant and wild-type embryos in the absence of neurotrophins. After 24 hours, cohorts of neurons were identified and recorded on graph paper (Vogel and Davies, 1991); at this time neurotrophins were added to some of the cultures at a concentration of 2 ng/ml. These cohorts of neurons were monitored daily throughout the culture period.

TABLE 2

| | % Survival of E12.5 DRG Neuron Cohorts | | | | |
|---|---|---|---|---|---|
| Genotype | NTFs | 48 | 72 | 96 | 120 |
| NF1(−/−) | (−) | 87.8 | 80.5 | 75.5 | 70.7 |
| | (−) | 74.2 | 70.9 | 61.3 | 54.8 |
| | all 4 | 88.9 | 79.8 | 71.7 | ND |
| | all 4 | 93.8 | 90.8 | 81.5 | ND |
| wt | (−) | 11.1 | 0 | 0 | ND |
| | (−) | 15.4 | 0 | 0 | ND |
| | all 4 | 89.6 | 75.3 | 75.3 | ND |

EXAMPLE 3

Methods for Embryonic Mouse Neuron Cultures

Tissue Culture Dishes—Nunclon, 35 mm, with air vents

A. Coat overnight with 0.5 mg/ml polyornithine (Sigma) in 0.15 m borate buffer pH 8.6 (~1.5 ml polyornithine solution per dish).

B. Wash dishes×3 with sterile ddH$_2$O; air dry in Tissue Culture (TC) hood.

C. Add (Gibco) laminin solution (20 mg/ml in PBS (−)) to enter of each dish (covering area of 5×5 mm grid) ~100 ml/dish.

D. Incubate laminin solution on dishes at 37° C. (in TC incubator) for at least 4 hrs (can be overnight).

Trypsin Solution

Trypsin(Gibco Powder)

A. store as 1% solution in ddH$_2$O; 200 ml aliquots @-20° C.

B. Dilute to 0.1% in PBS (−) for ganglion dissociation.

Culture Medium

A. F14+5% heat-inactivated Horse Serum (JRH Biosci)+ 5% heat-inactivated fetal calf serum (Hyclone)+1 mm glutamine (Gibco)+0.5×pen-strep (Gibco).

B. Ham's F14 medium special order from Gibco; make up 1 liter at a time from powder (1.5 g sodium bicarbonate (add first to ddH$_2$O)/liter).

C. 1×F14 liquid is good for ~1 month at 4° C.

D. Neuron culture medium with serum is good for ~2 weeks at 4° C.

Equipment

Pasteur pipettes—sterile, cotton-plugged; fire-polish for trituration. No need to siliconize/preferably coat insides with serum-containing medium to prevent tissue sticking.

Tungsten needles—electrolytically sharpen in 5 m KOH.

Needle holders—pin clamps from Ted Pella Co.01.

EXAMPLE 4

E13.5 Mouse Dorsal Root Ganglion NGF Dose Response

The following example illustrates the NGF Dose-Response curve for E13.5 DRG Neurons Isolated from NF1 ko and wt mice A. Coat vented 35 mm nunclon TCP dishes with polyornithine (0.5 mg/ml in 0.15M borate buffer pH 8.6) overnight @ room temp.

B. Wash dishes×3 with sterile ddH$_2$O; air dry in hood.

C. Incubate with laminin (20 mg/ml) in PBS @ 37° C. for 3.5 hrs.

Mouse embryos E13.5—35A-NF1 mutant small eyes hydrothorax Medium: F14 (Gibco Formula #78-5248EA)+10% HIFCS+2 mm glutamine+0.5×pen/strep.

A. For each embryo, dissect out 16 DRG in L15/1×pen-strep, clean off roots & mesenchyme, collect in separate 15 ml conical-bottom tubes.

B. Incubate @ 37° C. in 0.1% trypsin/PBS for 18 min.

C. Add 5 ml medium, spin @ ½ speed/dump off supernatant & repeat.

D. Dump off supernatant, add ~1 ml medium & triturate×6 with a serum-coated, fire-polished Pasteur pipette.

E. Distribute each cell suspension evenly among 10 dishes: add neurotrophins immediately as follows.

1 none (no neurotrophins)
1 20 ng/ml
1 2 ng/ml
2 200 pg/ml
2 20 pg/ml
2 2 pg/ml
1 0.2 pg/ml.

Counts

| Culture | | | 24 hrs 11/7 |
|---|---|---|---|
| NF35A-DRG | | none | 165 |
| ko/ko | NGF | 20 ng/ml | 242 |
| | NGF | 2 ng/ml | 278 |
| | NGF | 200 pg/ml (1) | 365 |
| | | (2) | 381 |
| | | | 397 |
| | NGF | 20 pg/ml (1) | 736 |
| | | (2) | 710 |
| | | | 684 |
| | NGF | 2 pg/ml (1) | 249 |
| | | (2) | 254 |
| | | | 259 |
| | NGF | 0.2 pg/ml | 208 |
| NF35B-DRG | | none | 0 |
| wt | NGF | 20 ng/ml | 389 |

| Culture | | | 24 hrs 11/7 |
|---|---|---|---|
| | NGF | 2 ng/ml | 418 |
| +/ko | NGF | 200 pg/ml (1) | 603 |
| | | (2) | 594 |
| | | | 584 |
| | NGF | 20 pg/ml (1) | 211 |
| | | (2) | 228.5 |
| | | | 246 |
| | NGF | 2 pg/ml (1) | 0 |
| | | (2) | 0 |
| | NGF | 0.2 pg/ml | 0 |

EXAMPLE 5

E13.5, E15.5

Superior Cervical Ganglion Neurons-Mouse Neurotrophin-Independent Survival and NTF Responsiveness in E13.5 SCG Neurons Isolated from P53 ko and wt Mice A. Coat vented 35 mm nunclon TCP dishes with polyornithine 0.5 mg/ml in 0.15 m borate buffer pH8.6) overnight @ room temp.

B. Wash dishes×3 with sterile ddH$_2$O; air dry in hood incubate with laminin (20 ngml) in PBS @ 37° C. O/N.

Mouse Embryos E13.5 "P53-7A-K".

A. or each embryo, dissect out both SCG in L15/1×pen-strep, clean off mesenchyme & roots, collect in separate 15 ml cervical-bottom tubes, rinse×2 in PBS.

B. Incubate @ 37° C. in 0.1% trypsin/PBS 20 min.

C. Add 5 ml medium, spin @ ½ speed/dump off supernatant & repeat.

D. Dump off supernatant, add ~1 ml medium & triturate× 6° C. a serum-coated, fire-polished Pasteur pipette.

E. Plate each cell suspension among 3 dishes, do not add neurotrophins yet.

F. After 24 hrs counts, add NGF (1 gn/ml) or NT3 (2 ng/ml) to cultures.

P53-16 Neurotrophin Independent Survival and NTF Responsiveness in E15.5 SCG Neurons Isolated from P53 ko and wt Mice.

A. Coat vented 35 mm nunclon TCP dishes with polyornithine 0.5 mg/ml in 0.15 m borate buffer pH8.6) overnight @ room temp.

B. Wash dishes×3 with sterile ddH$_2$O; air dry in hood.

C. ncubate with laminin (20 mg/ml) in PBS @ 37° C. O/N.

Mouse Embryos E15.5 "P5316 A-E"

A. For each embryo, dissect out one SCG in 115/1×pen-strep, clean off mesenchyme & roots, collect in separate 15 ml conical-bottom tubes.

B. Rinse×2 in PBS.

C. Incubate @ 37° C. in 0.1% trypsin/PBS 24 min.

D. Add 5 ml medium, spin @ ½ speed/dump off supernatant & repeat.

E. Dump off supernatant, add ~1 ml medium & triturate ×6 with a serum-coated, fire-polished pasteur pipette.

F. Plate each cell suspension evenly among 5 dishes, add neutrophins after 5 hrs in the following amounts, NGF 1 ng/ml, NT3 2 ng/ml.

|  |  |  | Counts |  |  |  |  |
|---|---|---|---|---|---|---|---|
| Culture | 24 HRS | 48 HRS | av. % surv | 72 HRS | av. % surv | 96 HRS | av. % surv |
| P5316A +/ko |  |  |  |  |  |  |  |
| 1. 0 | 204 |  |  |  |  |  |  |
| 2. 0 | 225 |  |  |  |  |  |  |
| 3. NGF | 329 |  |  |  |  |  |  |
| 4. NGF | 237 |  |  |  |  |  |  |
| 5. NT3 | 319 |  |  |  |  |  |  |
| P5316B ko/ko |  |  |  |  |  |  |  |
| 1. 0 | 235 (100) | 253 (108) |  | 248 (106) |  | 152 (65) |  |
| 2. 0 | 218 (100) | 262 (120) | 114 | 185 (85) | 96 | 120 (55) | 60 |
| 3. NGF | 251 (100) | 359 (143) |  | 350 (139) |  | 307 (122) |  |
| 4. NGF | 239 (100) | 325 (136) | 140 | 333 (139) | 139 | 312 (131) | 127 |
| 5. NT3 | 297 (100) | 367 (124) |  | 299 (101) |  | 162 (55) |  |
| P5316C +/ko |  |  |  |  |  |  |  |
| 1. 0 | 176 (100) | 135 (77) |  | 60 (34) |  | 33 (19) |  |
| 2. 0 | 199 (100) | 177 (89) | 83 | 76 (38) | 36 | 31 (16) | 18 |
| 3. NGF | 244 (100) | 220 (90) |  | 212 (87) |  | 186 (76) |  |
| 4. NGF | 271 (100) | 259 (96) | 93 | 242 (89) | 88 | 175 (72) | 74 |
| 5. NT3 | 296 (100) | 283 (96) |  | 160 (54) |  | 69 (23) |  |
| P5316D +/ko |  |  |  |  |  |  |  |
| 1. 0 | 181 (100) | 132 (73) |  | 79 (44) |  | 25 (14) |  |
| 2. 0 | 168 (100) | 114 (68) | 71 | 53 (32) | 38 | 25 (12) | 13 |
| 3. NGF | 237 (100) | 226 (95) |  | 201 (85) |  | 214 (90) |  |
| 4. NGF | 253 (100) | 241 (95) | 95 | 215 (85) | 85 | 223 (88) | 89 |
| 5. NT3 | 321 (100) | 297 (93) |  | 164 (51) |  | 47 (15) |  |
| P5316E +/+ |  |  |  |  |  |  |  |
| 1. 0 | 190 (100) | 110 (58) |  | 32 (17) |  | 13 (7) |  |
| 2. 0 | 205 (100) | 118 (58) | 58 | 48 (23) | 20 | 12 (6) | 7 |
| 3. NGF | 312 (100) | 270 (100) |  | 264 (85) |  | 270 (87) |  |
| 4. NGF | 287 (100) | 262 (100) | 82 | 225 (78) | 82 | 241 (84) | 86 |
| 5. NT3 | 342 (100) | 285 (100) |  | 114 (33) |  | 40 (12) |  |

EXAMPLE 6

E12 Mouse Trigeminal Ganglion

CRR Neurotrophic Factor-Independent Survival and NTF Responsiveness in E12.0 Trigeminal Neurons Isolated from NF ko and wt Mice A. Coat 35 mm vented Nenclon dishes with polyornithine 6.5 mg/ml in 0.15 m borate buffer pH8.6) overnight at room temp.

B. Wash dishes×3 with sterile ddH$_2$O; air dry in hood, incubate with laminin (20 mg/ml in PBS) 4 hrs @ 37° C.

C. Medium: F14+10% H1HS+5% HIFCS+0.5×pen/strep+2 mM glutamine.

D. Mouse embryos: (CR12A-E E11.5/E12.)
  a: NF—small PE of eye hydrothorax
  b: WT
  C: NF—small PE of eye hydrothorax
  D: Wt
  E: WT—younger than others E. Dissect out both trigeminal ganglia in L15, clean off mesenchyme, collect in separate 15 ml conical-bottom tubes.

F. Rinse ganglia×2 in PBS.

G. Incubate @ 37° C. in 0.125% trypsin/PBS 15 min.

H. Add 5 ml F14+10% H1HS to each tube, spin @ ½ speed 5 min.

I. Dump off F14+H1HS, add ~1 ml F14+H1HS+H1FCs to each tube.

J. Triturate×10 with a serum-coated, fire-polished pasteur pipette.

K. Distribute cell suspension evenly among 6 (A,B) or 5(C,D,E) dishes Plate @ 2:30 p.m.; add neurotrophins immediately.

| For A&B: | 1 | none | For C,D,E: | 1 | none |
|---|---|---|---|---|---|
|  | 1 | NGF 1 ng/ml |  | 1 | NGF 1 ng/ml |
|  | 1 | BDNF 1 ng/ml |  | 1 | BDNF 1 ng/ml |
|  | 1 | NT3 1 ng/ml |  | 1 | NT3 1 ng/ml |
|  | 1 | NT5 1 ng/ml |  | 1 | NT5 1 ng/ml |
|  | 1 | ALL41 ng/ml |  | 1 | ALL41 ng/ml |

| Culture | CR12 Counts | | | | | |
|---|---|---|---|---|---|---|
| | 24 HRS | % of all 4 | 48 HRS | % of all 4 | 72 HRS | % of all 4 |
| CR12A NF ko/ko | | | | | | |
| 0 | 31 | 67.4 | 43 | 52.4 | 39 | 43.4 |
| NGF | 44 | 95.7 | 82 | 100 | 71 | 78.9 |
| BDNF | 61 | 132.6 | 113 | 137.8 | 106 | 117.8 |
| NT3 | 41 | 89.1 | 84 | 102.4 | 62 | 68.9 |
| NT5 | 46 | 100 | 72 | 87.8 | 64 | 71.1 |
| ALL 4 | 46 | 100 | 82 | 100 | 90 | 100 |
| CR12B +/ko | | | | | | |
| 0 | 136 | 44.2 | 88 | 21 | 16 | |
| NGF | 279 | 90.6 | 523 | 124.5 | 228 | |
| BDNF | 203 | 65.9 | 92 | 21.9 | | |
| NT3 | 251 | 81.5 | 101 | 24 | | |
| NT5 | 95 | 30.8 | 52 | 12.4 | | |
| ALL 4 | 308 | 100 | 420 | 100 | | |
| CR12C ko/ko | | | | | | |
| 0 | 50 | 45.5 | 60 | 40.8 | 62 | 42.8 |
| NGF | 53 | 48.2 | 79 | 53.7 | 77 | 53.1 |
| BDNF | 87 | 79.1 | 134 | 91.2 | 157 | 108.3 |
| NT3 | 94 | 85.5 | 97 | 66 | 109 | 75.2 |
| NT5 | N.D. | | | | | |
| ALL 4 | 110 | 100 | 147 | 100 | 145 | 100 |
| CR12D +/+ | | | | | | |
| 0 | 209 | 44.9 | 66 | 9.4 | | |
| NGF | 436 | 93.8 | 679 | 96.4 | | |
| BDNF | 278 | 59.8 | 149 | 21.2 | | |
| NT3 | 481 | 103.4 | 191 | 27.1 | | |
| ALL 4 | 465 | 100 | 704 | 100 | | |

EXAMPLE 7

E12.5 Mouse Nodose Ganglion
CR10 Neurotroghic Factor—Independent Survival and NTF-Responsiveness in E12.5 Nodose Neurons Isolated from NF ko and wt Mice A. Incubate 35 mm vented nunclon dishes with polyornithine 0.5 mg/ml in 0.15M borate buffer pH8.6) overnight at room temp.
B. Wash dishes×3 with sterile ddH₂O; air dry in hood, incubate with laminin (20 ng/ml in PBS) 6 hrs at 37° C. Medium: F14+10% H1HS+5% H1FCS+0.5×pen strep+2 mM glutamine
Mouse embryos E12.5 CR10A—wt
CR10B—"NF" very small PE of eye hydrothorax.
C. Eissect out both nodose ganglia from each embryo in L15, clean off mesenchyme & nerve roots, collect in separate 15 ml conical-bottom tubes.
D. Rinse ganglia×2 in PBS.
E. Incubate @ 37° C. in 0.125% trypsin/PBS 20 min.
F. Add 5 ml F14+H1HS to each tube, spin @ ½ speed 5 min.
G. Triturate×8 with a serum-coated, fire-polished pasteur pipette.
H. Distribute each cell suspension evenly among 4 dishes (~½ ganglion/dish).
I. Plate at ~4:00 pm, add neurotrophins immediately:
1 no neurotrophins (none)
1NGF 1 ng/ml
1BDNF 1 ng/ml
1NT3 1 ng/ml
J. Add 500 ml medium, fresh neurotrophins.

| Culture | Counts | | |
|---|---|---|---|
| | 24 HRS | 48 HRS | 72 HRS |
| wt CR10A | | | |
| none | 18 | 16 | 14 |
| NGF | 98 | 86 | 78 |
| BDNF | 230 | 199 | 131 |
| NT3 | 20 | 16 | 13 |
| NF CR10B | | | |
| none | 146 | 146 | 134 |
| NGF | 218 | 244 | 225 |
| BDNF | 341 | 343 | 237 |
| NT3 | 186 | 203 | 164 |

EXAMPLE 8

E9/El10 Chick Dorsal Root Ganglia+Percoll
Method to Obtain Pure Neurons+% Supported by Each Neurotrophin
CHKN 1: Dose-Response Curve for Neurotrophins/E9 Chick DRG A. Coat 35 mm nunclon dishes with poly-D-ornithine (0.5 ng/ml in 0.15 m borate buffer pH8.6) overnight at room temp.
B. Vash dishes×3 with sterile ddH₂O; air dry in hood.
C. Incubate with laminin (20 pg/ml) in PBS @ 37° C., 5 hrs. Medium: F14+10% H1HS+5%H1FCS+0.5% pen/strep+2 mMgl.
Chicken embryos: E9 STG 35 (H & H)
D. Dissect out 60 DRG (2 embryos) in L15—clean off esenchyme.
E. Rinse DRG×2 in PBS.
F. Incubate @ 37° C. in 0.25% trypsin (1 lml total) PBS 40 min.
G. Add 10 ml F14+H1Hs.
H. Spin 5 min @ ½ speed, dump off supernatant.
I. Add ~½ ml F14+H1HS+H1FCS.
J. Triturate×12 with fire- polished serum-coated Pasteur pipette.
K. Plate cell suspension so that ~1.25–1.5 ganglia/dish in 2 ml F14+10% H1Hs+5% H1FCS that contains factors.
L. Control=no factors.

| Dishes: | NGF | 5 ng/ml × 2 | NT5 | 5 ng/ml × 2 |
|---|---|---|---|---|
| | | 500 pg/ml × 2 | | 500 pg/ml × 2 |
| | | 50 pg/ml × 2 | | 50 pg/ml × 2 |
| | | 5 pg/ml × 2 | | 5 pg/ml × 2 |
| | BDNF | 5 ng/ml × 2 | | |
| | | 500 pg/ml × 1 | | |
| | | 50 pg/ml × 2 | | |
| | | 5 pg/ml × 2 | | |
| | NT3 | 5 ng/ml × 2 | | |
| | | 500 pg/ml × 2 | | |
| | | 50 pg/ml × 2 | | |
| | | 5 pg/ml × 2 | | |

NGF(500 pg/m l)+BDNF(500 pg(ml)
All factors @ 5 ng/ml×2
All factors @ 500 pg/ml×2
NGF, BDNF, NT3 @ 5 ng/ml (frozen in medium)
NGF, BDNF, NT3 @ 500 pg/ml(frozen in medium)
100% S.I.P=9 parts per coll+1 part 10×CMF–PBS
74% SIP=3.7 ml 100% SIP+1.3 ml 1×CMF—PBS
CHKN-11 Separation of Neurons/Non-neurons from E10 Chick DRG using percoll gradient/responses of neurons to neurotrophins A. Coat 35 mm nunclon dishes with poly-D-ornithine 6.5 mg/ml) in 0.15M borate buffer pH8.6) overnight at room temp.
B. Wash dishes×3 with sterile ddH₂O; air dry in hood.
C. Incubate with laminin (20 mg/ml in PBS) @ 37° C. 6 hrs. Medium: F14+10% H1HS+5% H1FCs+0.5×pen/strep+2 mM glutamine. Chicken embryos E10 H & H stg 36
D. Dissect out 30 DRG (1 embryo ) in L15—clean off mesenchyme, collect in 15 ml conical-bottom tube.
E. Rinse DFG×2 in PBS.
F. Incubate @ 37° C. in 0.25% trypsin (1 ml total) PBS 45 min.
G. Add 10 ml F14+H1Hs, pellet ganglia @ ½ speed 4 min.
H. Dump off supernatant, add 1 ml F14+H1HS+H1FCs.
I. Triturate×10 with serum-coated, fire-polished Pasteur pipette.
J. Eellet cells @ ½ speed (~4 min); remove supernatant & resuspend cells in 1.5 ml 0.05% trypsin/PBS.
K. Add 1.5 ml 74% standard isoosmotic Percoll; layer ~1 ml PBS on top.
L. Centrifuge 14 min @ 400 g @ 20–25° C.
M. Remove nonneuronal cells at Percoll/PBS interface, remove all Percoll.
N. Wash pelleted neurons×2 in F14+H1HS+H1FCS; spin down @ ½ speed.
O. Remove supernatant; resuspend neurons in ~1 ml F14+H1Hs+H1FCS.
P. Distribute neurons equally among 10 dishes.
Q. Add neurotrophins immediately.
2 no neurotrophins (none)
2 NGF 500 pg/ml
2 BDNF 500 pg/ml
2 NT3 500 pg/ml
2 all neurotrophins 500 pg/ml

| Culture | | | #Neurotrophins 48 Hours |
|---|---|---|---|
| none | (1) | | 3 |
| | (2) | | 3 |
| NGF | 500 pg/ml | (1) | 104 |
| | | (2) | 103 |
| BDNF | 500 pg/ml | (1) | 119 |
| | | (2) | 117 |
| NT3 | 500 pg/ml | (1) | 47 |
| | | (2) | 48 |
| All3 | 500 pg/ml | (1) | 244 |
| | | (2) | 229 |

EXAMPLE 9

E10 Chick0 Nodose Ganglia+% Supported by each Neurotrophin
CHKN-12 Survival Response of E10 Chick Nodose Neurons to Neurotrophins NGF, BDNF, NT-3, and NT-5

A. Coat 35 mm nunclon dishes with polyornithine (0.5 mg/ml in 0.15 m borate buffer pH 8.6) overnight at room temp.
B. Wash dishes×3 with sterile ddH₂O air dry in hood.
C. ncubate with laminin (20 mg/ml in PBS) @ 37° C. 4 hrs. Medium: F14+10% H1HS+5% H1FCS+0.5×pen/strep+2 mM glu Chicken embryos E10 H & H STG 36
D. Dissect out 6 nodose ganglia in L15; clean off mesenchyme, collect in 15 ml conical bottom tube.
E. Rinse ganglia×2 in PBS.
F. Incubate @ 37° C. in 0.25% trypsin/PBS 40 min.
G. Add ~1 ml F14+H1HS+H1FCS triturate×10C serum-coated, add 5 ml F14–H1HS, spin @ ½ speed 5 min. fire-polished Pasteur pipette.
H. Distribute cell suspension evenly among 10 dishes (~½ ganglian/Dish).
I. Add neurotrophins immediately:
2 no neurotrophins (none)
1 NGF 2 ng/ml
1 BDNF 2 ng/ml
1 NT3 2 ng/ml
1 NT5 2 ng/ml
1 All 4 neurotrophins 2 ng/ml
1 All 4 neurotrophins 250 pg/ml
1 BDNF+NT3 2 ng/ml
1 BDNF+NT3 250 pg/ml

| Counts | | #Neurons | | |
|---|---|---|---|---|
| Culture | | 48 hrs. | 72 hrs | 96 hrs. |
| E10 nodose | none(1) | 1 | none | none |
| | (2) | none | none | none |
| NGF | 2 ng/ml | none | none | none |
| BDNF | 2 ng/ml | 12 | 14 | 13 |
| NT3 | 2 ng/ml | 13 | 14 | 14 |
| NT5 | 2 ng/ml | 1 | 2 | 1 |
| All 4, | 2 ng/ml | 44 | 45 | 33 |
| | 250 pg/ml | 32 | 42 | 35 |
| BDNF + NT3 | 2 ng/ml | 30 | 31 | 21 |
| | 250 pg/ml | 24 | 15 | 11 |

EXAMPLE 10

Candidate Substance Screening Assays

These assays can be performed on any vertebrate sensory and sympathetic neuronal cultures although most information is available for mouse, chick, and rat. The present inventors' work that has elucidated the role of neurofibromin in survival, was done in mouse for technical and genetic reasons, however for any high volume screening the proposed assays can probably be best done in the chick since the cost, manipulations, and speed are most advantageous.

All assays rely on cultures of neurons from diverse sympathetic and sensory ganglia [i.e., DORSAL ROOT, TRIGEMINAL, NODOSE, SUPERIOR CERVICAL, SYMPATHETIC TRUNK] into culture dishes. Typically, these studies are done in the presence of serum, however, serum free protocols are available and may be desirable in circumstances where that potential activity of a compound may be masked or compromised in the presence of serum. In general embryos of specific embryonic stages are prepared and specific ganglia dissected out and pooled. The timing of dissection will depend on the embryo species. For most preliminary studies, dorsal root ganglion (DRG) neurons will be the substrate of choice as they are relatively easy to dissect and are present in greatest numbers (approx. 36–40 per embryo versus one pair in the other instances). The most reliable assay would be for survival of mature neurons that require neurotrophin immediately upon culturing (mouse: E13.0 DRG); chick stage E6–E7 DRG; FIG. 1–FIG. 7A. Upon dissociation, equivalent numbers of cells are Elated in the presence of the appropriate neurotrophin (in the case of DRG, NGF would provide the greatest survival) and after neuron attachment to the substrate (12–24 hrs), the media can be changed for media (1) without neurotrophin; (2) with neurotrophin, (3) with the compounds that are to be tested and, (4) with compounds to be tested (various conditions) plus neurotrophin. The neurotrophin free cultures will provide the baseline (regative control); these cultures will diminish in cell number rapidly [24–48 hrs]. The cultures with added neurotrophin will provide the positive control and the capacity of these cultures to survive will determine the 100% success line. Compounds plus neurotrophin will provide several relevant pieces of information: 1) synergy: genetic inactivation of neurofibromin renders the survival signalling pathway constitutively active but it is stil susceptible to hyperactivity through the normal neurotrophin mediated activation (i.e., in one case, the leak is permitted, in the other, the water pressure is increased). Similarly, it could be envisioned that compounds may unexpectedly not only inactivate neurofibromin function as a negative regulator, but additionally, enhance the flow of signalling. This increase would be recorded as an increased survival in numbers and/or time with respect to the neurotrophin alone cultures. 2) Conversely, certain compounds may have neurofibrorin inactivation effect but also may be toxic to cells. This condition can only be unmasked in the presence of neurotrophin. The two compounds together would exhibit reduced survival compared to neurotrophin alone.

As noted, DRG cultures would be the easiest to obtain in considerable numbers for quantitative assays. The cultures are routinely done on tissue culture plates that have engraved grids that permit neuron counts to be made on a routine and reliable basis [see Tables 1A, 1B & 2]. It may be possible that an even easier (and certainly less rigorous) assay may be adopted to perform preliminary screening of compounds. This assay is referred to as an explant assay. In this case pieces of ganglia are cultured in wells. In the presence of neurotrophins in the media, the neurons mature and project neurites in what gives a halo effect surrounding the bit of ganglion. In the absence of neurotrophin, neurons do not mature and sprout neurites.

Neurons undergo at least three phases of neurotrophin responsiveness that can be seen in vivo and in culture. Neuronal precursors do not look like neurons and do not rely on neurotrophins for their survival. When cultured, these cells do not initially require neurotrophins in their media but acquire the dependence over time. Immature neurons, which coincide with the period when in vivo they extend projections to their sites of innervation, is a period when neurons begin to acquire neuronal morphology and also to respond to neurotrophins. Neuronal cultures from this period contain some cells that do not yet require neurotrophins, and cells that can respond to multiple neurotrophins. Finally, mature neurons have a quite distinctive morphology (i.e., long, bipolar projections; refractile; enlarged cell body) and mainly have a requirement for one specific neurotrophin. These cells require continuous neurotrophin in their media in order to survive.

Thus, for compounds which may have a short half-life, the use of mature neurons in the assay will be most useful. However, to test effective half-life, or to test compounds whose effective dosage must be gradually incremented for purposes of cellular adaptation the use of immature cultures will be very useful.

After preliminary studies with DRG explants and/or cultures, the availability of different ganglia (nodose, trigeminal, sympathetic) and various species will permit the elaboration of dose ranges, toxicity ranges, and responsiveness to diverse neurotrophins, since ganglia consist of heterogeneous subpopulations of neurons that respond to different neurotrophins.

A verb time consuming and labor intensive aspect of the dissociated culture assay is the actual quantitation via cell counts. Initially, the cells are plated on dishes which have been outlined with a grid. All cells within the grid are counted and then subsequent periodic counts are made to determine the survival of a defined subpopulation of neurons [Tables 1A, 1B & 2]. It is contemplated that existing technology may be adapted to accelerate this process. The use of computer software and imaging that is currently in use for automated cell microinjectors could be used to perform and "mark" the initial cell counts. Thereafter, the gridded plates could be placed on the counted and the surviving neurons could be counted electronically. Similarly adapted technology would permit the automated assay of halo appearance in the explant assay.

The details of dissection, explant culturing, or dissociated cultures are well established and do not, of themselves, constitute the present invention. The details of the survival assays are relevant but only in dependence of the conditions imposed by this assay whereby neurons are subjected to compounds that may relieve them of the requirement for added neurotrophins to survive.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Andersen J K; Frim D M; Isacson O; Breakefield X O. 1993. Herpesvirus-mediated gene delivery into the rat brain: specificity and efficiency of the neuron-specific enolase promoter. Cell Mol Neurobiol, Oct 1993, 13 (5) p503–15.

Andersen J K; Garber D A; Meaney C A; Breakefield X O. 1992. Gene transfer into mammalian central nervous system using herpes virus vectors: extended expression of bacterial lacZ in neurons using the neuron-specific enolase promoter. Hum Gene Ther Oct 1992, 3 (5) p487–9S.

Ballester R; D Marchuk; M Boguski; A Saulino; R Letcher, M Wigler; F S Collins. 1990. The NF1 locus encodes a protein functionally related to mammalian GAP and yeast IRA proteins. Cell 63: 851–859.

Beitel G; E Clark; H R Horvitz. 1990. The *Caenorhabditis elegans ras* gene 1Et-60 acts as a switch in the pathway of vulval induction. Nature 348: 503–509.

Birren S J; L C Lo; D J Anderson. 1993. Sympathetic neurons undergo a developmental switch in trophic dependence. Development 119: 597–610.

Boguski M S; F McCormick. 1993. Proteins regulating ras and its relatives. Nature 366: 643–654.

Bollag G; F. McCormick. 1991. Differential regulation of rasGAP and neurofibromatosis gene product activities. Nature 351, 576–579.

Bonfini L; C A Karlovich; C Dasgupta; U Banerjee. 1992. The son of sevenless gene product: a putative activator of ras. Science 255: 603–606.

Borasio G D; J John; A Wittinghofer; Y A Barde; M Sendtner; R Heumann. 1989. ras p21 protein promotes survival and fiber outgrowth of cultured embryonic neurons. Neuron 2: 1087–1096.

Borasio G D; A Markus; A Wittinghofer; Y A Barde; R. Heumann. 1993. Involvement of ras p21 in neurotrophin-induced response of sensory, but not sympathetic neurons. J. Cell Biol. 121: 665–672.

Bourne H R; D A Sanders; F McCormick. 1991. The GTPase superfamily: conserved tructure and molecular mechanism. Nature 349:117–127.

Brannan C I; A S Perkins; K S Vogel; N Ratner; M L Nordlund; S W Reid; A M Buchber ; N A Jenkins; L F Parada; N G Copeland. 1994. Targeted disruption of the neurofibromatosis type-1 gene leads to developmental abnormalities in heart and various neural crest-derived tissues. Genes Dev. 8: 1019–1029.

Breakefield X O; DeLuca N A. 1991. Herpes simplex virus for gene delivery to neurons. New Biol Mar 1991, 3 (3) p203–18.

Buchberg A M; L S Cleveland, N A Jenkins; N G Copeland. 1990. Sequence homology shared by neurofibromatosis type-1 gene and IRA-1 and RA-2 negative regulators of the RAS cyclic AMP pathway. Nature 347: 291–294.

Buchman V L; A M Davies. 1993. Different neurotrophins are expressed and act in a developmental sequence to promote the survival of embryonic sensory neurons. Development 118: 989–1001.

Clarke A R; E R Maandag; M van Roon; N M T van der Lugt; M van der Valk; M L Hooper; A Berns; H te Riele. 1992. Requirement for a functional Rb-1 gene in murine development. Nature 359: 328–330.

Coughlin M D; M B Collins. 1985. Nerve growth factor-independent development of embryonic mouse sympathetic neurons in dissociated cell culture. Dev. Biol. 110: 392–401.

D'Amico-Martel A; D M Noden. 1983. Contributions of placodal and neural crest cells to avian peripheral ganglia. Am. J. Anat. 166:445–468.

D'Arcangelo G; S Halegoua. (1993). A Branched Signaling Pathway for Nerve Growth Factor Is Revealed by Src-, Ras-, and Raf-Mediated Gene Inductions. Molecular and Cellular Biology, 13 (6), 3146–3155.

Daston M M; Ratner. 1992. Neurofibromin, a predominantly neuronal GTPase activating protein in the adult, is ubiquitously expressed during development. Dev. Dynamics 195: 216–226.

Daston M M; Scrable; M Nordlund; A K Sturbaum; L M Nissen; N Ratner. 1992. The protein product of the neurofibromatosis type 1 gene is expressed at highest abundance in neurons, schwann cells, and oligodendrocytes. Neuron 8: 415–428.

Davies A M; A Lumsden. 1984. Relation of target encounter and neuronal death to nerve growth factor responsiveness in the developing mouse trigeminal ganglion. J. Comp. Neurol. 223: 124–137.

Davies A M; C Bandtlow; R Heumann; S Korsching; H Rohrer; H Thoenen. Timing and site of nerve growth factor synthesis in developing skin in relation to innervation and expression of the receptor. nature 326: 353–358.

Davies A M; A Horton; L E Burton; C Schmelzer; R Vandlen; A Rosenthal. 1993. Neurotrophin 4/5 is a mammalian-specific survival factor for distinct populations of sensory neurons. J, Neurosci. 13: 4961–4967.

Davies A M. 1994. Intrinsic programmes of growth and survival in developing vertebrate neurons. Trends Neurosci. 17: 195–199.

DiCicco-Bloom E; E Townes-Anderson; I B Black. 1990. Neuroblast mitosis in dissociated culture: regulation and relationship to differentiation. J. Cell Biol. 110: 2073–2086.

DiCicco-Bloom E; W J Friedman; I B Black. 1993. NT-3 stimulates sympathetic neuroblast proliferation by promoting precursor survival. neuron 11: 1101–1111.

Donehower L A; M Harvey; B L Slagle; M J McArthur; C A Montgomery; J S Butel; A Bradley. 1992. Mice deficient for p53 are developmentally normal but susceptible to spontaneous tumors. Nature 356 215–221.

Ernsberger U; H Rohrer. 1988. Neuronal precursor cells in chick dorsal root ganglia: differentiation and survival in vitro. Dev. Biol. 126: 420–432.

Gutmann D H; F S Collins. 1993. The neurofibromatosis type 1 gene and its protein product, neurofibromin. Neuron 10: 335–343.

Han M; R Aroian; P W Sternberg. 1990. The let-60 locus controls the switch between vulval and non-vulval cell types in C. elegans. Genetics 126; 899–913.

Han M; A Golden; Y Han; P W Sternberg. 1993. C. elegans lin-45 raf gene participates in let-60 ras-stimulated vulval differentiation. Nature 363: 133–140.

Huynh D P; T Nechiporuk; S M Pulst. 1994. Differential expression and tissue distribution of type I and type II neurofibromins during mouse fetal development. Dev. Biol. 161: 538–551.

Jacks T; A Fazeli; E M Schmitt; R T Bronson; M A Goodell; R A Weinberg. L992. Effects of a Rb mutation in the mouse. Nature 359: 295–300 .

Jacks T; T S Shih; E M Schmitt; R T Bronson; A Bernards; R A Weinberg. :L994. Tumour predisposition in mice heterozygous for a targeted mutation in Nf1. Nature Genet. 7: 353–361.

James G L; J L Goldstein; M S Brown; T E Rawson; T C Somers; R S McDowell; C W Crowley; B K Lucas; A D Levinson; J C Marsters. 1993. Benzodiazepine peptidomimetics: potent inhibitors of ras farnesylat: on in animal cells. Science 260: 1937–1942.

Johnson M R, J E DeClue; S Felzmann; W C Vass; G Xu; R White; D R Lowy. 1994 Neurofibromin can inhibit ras-dependent growth by a mechanism independent of its GTPase-accelerating function. Mol. Cell. Biol. 14: 641–645.

Kaplan D R; B L Hempstead; D Martin-Zanca; M V Chao; L F Parada. 1991a. The trk proto-oncogene product: a signal transducing receptor for nerve growth factor. Science 252: 554–558.

Kaplan D R; D Martin-Zanca; L F Parada. 1991b. Tyrosine phosphorylation and tyrosine kinase activity of the trk proto-oncogene p oduct induced by NGF. Nature 350: 158–160.

Kaplan, D R; R M Stephens. 1994. Neurotrophin signal transduction by the trk receptors. J. Neurobiol. 25: 1404–1417.

Kohl N E; S E Mosser; S J deSolms; E A Giuliani; D L Pompliano; S L Graham; R L Smith; E M Scolnick; A Oliff; J B Gibbs. 1993. Selective inhibition of ras-dependent transformation by a farnesyltransferase inhibitor. Science 260: 1934–1937.

Korsching S. 1993. The neurotrophic factor concept: a reexamination. J. Neurosci. 13: 2739–2748.

Korsching S; H Thoenen. 1988. Developmental changes of nerve growth factor levels in sympathetic ganglia and their target organs. Dev . Biol. 126: 40–46.

Kreidberg J A; H Sariola; J M Loring; M Maeda; J Pelletier; D Housman; R Jaenisch. 1993. WT-1 is required for early kidney development. Cell 74: 679–691.

Lawson S N; T J Biscoe. 1979. Development of mouse dorsal root ganglia: an autoradiographic and quantitative study. J. Neurocytol. 8: 265–274.

LeDouarin N M; C Kalcheim; M-A Teillet. 1992. The cellular and molecular basis of early sensory ganglion development. In "Sensory Neurons: Diversity, Development, and Plasticity", S. A. Scott, ed. Oxford University Press, New York. pp. 143–170.

Lee EY-HP; C-Y Chang; N Hu; Y-C J Wang; C-C Lai; K Herrup; W-H Lee; A Bradley. 1992. Mice deficient for Rb are nonviable and show defects in neurogenesis and haematopoiesis. Nature 359: 288–294.

Le Gal La salle G; Robert J J; Berrard S; Ridoux V; Stratford-Perricaudet L D; Perricaudet M; Mallet J. 1993. An adenovirus vector for gene transfer into neurons and glia in the brain. Science Feb 12 1993, 259 (5097) p988–90.

Legius E; D A Marchuk; F S Collins; T W Glover. 1993. Somatic deletion of the neurofibromatosis type 1 gene in a neurofibrosarcoma supports a tumor suppressor gene hypothesis. Nature Genet., 3: 122–126.

Li B-Q; D Kaplan; H Kung; T Kamata. 1992. Nerve growth factor stimulation of the ras-guanine nucleotide exchange factor and GAP activities. Science 256: 1456–1459.

Lowy D R; B Willumsen. 1993. Function and regulation of ras. Ann. Rev. Biochem. 62: 851–891.

Lindsay R M. 1994. Neurotrophic growth factors and neurodegene rative diseases: therapeutic potential of the neurotrophins and ciliary neurotrophic factor. Neurobiol Aging 15: 249–251.

Martin G A; Viskochil; G Bollag; P C McCabe; W J Crosier; H Haubruck; L Conroy; R Clark; P O'Connell; R M Cawthon; M A Innis; F McCormick. 990. The GAP-related domain of the neurofibromatosis type 1 gene product interacts with ras p21. Cell 63: 843–849.

Mittal S; A Cohen; D I Maysinger. 1994. In vitro effects of brain derived neurotrophic factor released from microspheres. Neuroreport 5: 2577–2582.

Ng N F L; E M Shooter. 1993. Activation of p21 ras by nerve growth factor in embryoic sensory neurons and PC12 cells. J. Biol. Chem. 268:25329–25333.

Olson L. 1993. Reparative strategies in the brain: treatment strategies based on trophic factors and cell transfer techniques. Acta Neurochir Suppl (Wien). 58: 3–7.

Onteniente ; Horellou P; Neveu I; Makeh I; Suzuki F; Bourdet C; Grimber G; olin P; Brachet P; Mallet J; et al. 1994. Cell-type-specific expression and regulation of a c-fos-NGF fusion gene in neurons and astrocytes of transgenic mice. Brain Res Mol Brain Res (NETHERLANDS) 21 (3–4) p225–34.

Oppenheim R W. 1991. Cell death during development of the nervous system. Ann. Rev. Neurosci. 14: 453–501.

Riccardi V M. 1991. Neurofibromatosis: Past, present, and future. N. Engl. J Med. 324: 1283–1285.

Rohrer H; 4 Thoenen. 1987. Relationship between differentiation and terminal mitosis: chick sensory and ciliary neurons differentiate after terminal mitosis of precursor cells, whereas sympathetic neurons continue to divide after differentiation. J. Neurosci. : 3739–3748.

Rohrer H; Hofer; R Hellweg; S Korsching; A D Stehle; S Saadat; H Thoenen. 1 88. Antibodies against mouse nerve growth factor interfere in vivo with the development of avian sensory and sympathetic neurones. Development 103: 545–552.

Rothman T P; M D Gershon; H Holtzer. 1978. The relationship of cell division to the acquisition of adrenergic characteristics by developing sympathetic ganglion cell precursors. Dev. Biol. 65: 322–341.

Rubin E. 1985. Development of the rat superior cervical ganglion: ganglion cell maturation. J. Neurosci. 5: 673–684.

Rylett R J; L R Williams. 1994. Role of neurotrophins in cholinergic-neurone function in the adult and aged CNS. Trends Neurosci (ENGLAND). 17: 486–490.

Seeburger J L; J E Springer. 1993. Experimental rationale for the therapeutic use of neurotrophins in amyotrophic lateral sclerosis. Exp Neurol (UNITED STATES). 124: 64–72.

Simon M A; B Dwtell D D; Dodson G S; Laverty T R; Rubin G M. 1991. Ras1 and a Dutative guanine nucleotide exchange factor perform crucial steps in signalling by the sevenless protein tyrosine kinase. Cell 67: 701–716.

Snider W D. 1994. Functions of the neurotrophins during nervous system development: what the knockouts are teaching us. Cell 77: 627–638.

Theiler K. 989. The House Mouse: Atlas of Embryonic Development. Springer-Verlag, New York.

Verdi J M; D J Anderson. 1994. Neurotrophins regulate sequential changes in eurotrophin receptor expression by sympathetic neuroblasts Neuron 13: 1359–1372.

Vogel K S. 1992. Origins and early development of vertebrate cranial seosory neurons. In "Sensory Neurons:Diversity, Development , and Plasticity", S. A. Scott, ed. Oxford University Press, New York. pp.171–193.

Vogel K S. 1993. Development of trophic interactions in the vertebrate peripheral nervous system. Mol. Neurobiol. 7: 363–382.

Vogel K S; A M Davies. 1991. The duration of neurotrophic factor independence in early sensory neurons is matched to the time course of target field innervation. Neuron 7: 819–830.

Weston J A. 1970. The migration and differentiation of neural crest cells. Adv. Morphogenesis 8: 41–114.

Williams B O; L Remington; D M Albert; R T Bronson; T Jacks. 1994. Cooperative tumorigenic effects of germline mutations in Rb and p53. Natur Genet. 7: 480–484.

Wright L L; T J Cunningham; A J Smolen. 1983. Developmental neuron death in the rat superior cervical sympathetic ganglion: Cell counts and ultrastructure. J. Neurocytol. 12: 727–738.

Xu, G., B Lin; K Tanaka; D Dunn; D Wood; R Gesteland; R White; R Weiss; F Tamanoi. 1990a. The catalytic domain of the neurofibromatosis type 1 gene product stimulates ras GTPase and complement ira mutants of S. cerevisiae. Cell 63: 835–841.

Xu G; P O'Donnell; D Viskochil; R Cawthon; M Robertson; M Culver; D Dunn; J tevens; R Gesteland; R White; R Weiss. 1990b. The neurofibromatosis type 1 gene encodes a protein related to GAP. Cell 62: 599–608.

Zimmerman L; Parr B; Lendahl U; Cunningham M; McKay R; Gavin B; Mann J; Vassileva G; McMahon A. 1994.

Independent regulatory elements in the nestin gene direct transgene expression to neural stem cells or muscle precursors. Neuron Jan 1994, 12 (1) p11–24.

Zwaagstra T C; Ghiasi H; Slanina S M; Nesburn A B; Wheatley S C; Lillycrop C; Wood J; Latchman D S; Patel K; Wechsler S L. 1990. Activity of herpes simplex virus type 1 latency-associated transcript (LAT) promoter in neuron-derived cells: evidence for neuron specificity and for a large LAT transcript. J Virol Oct 1990, 64 (0) p5019–28.

What is claimed is:

1. A method of identifying a substance that blocks neurofibromin action comprising the steps of:

(a) obtaining a substance suspected of blocking neurofibromin action;

(b) obtaining a culture of neural cells expressing neurofibromin;

(c) determining the survival of said neural cells in the presence of said substance and in the absence of neurotrophic factors;

(d) determining the survival of mouse neural cells lacking neurofibromin-1 (NF1) activity under identical conditions as in step (c), except in the absence of said substance; and (e) determining the survival of mouse neural cells lacking neurofibromin-1 (NF1) activity under identical conditions as in step (c);

wherein said substance has no effect on survival of neural cells of step (d) and (e); and wherein said substance enhances survival of neural cells of step (c) when compared to survival of said neural cells of step (c) in the absence of said substance, is indicative of blocking neurofibromin action.

2. The method of claim 1, further comprising the step of determining the effect of the presence of said substance on yeast IRA or mammalian GAP protein activity.

3. The method of claim 1, wherein said culture of neural cells is a culture of mouse neural cells.

4. A method of identifying a substance that blocks neurofibromin action comprising the steps of:

(a) obtaining neurons expressing neurofibromin;

(b) culturing said neurons in the presence of a candidate substance suspected of blocking neurofibromin action, but in the absence of neurotrophins;

(c) identifying neurons that survive in culture; and (d) determining the effect of said candidate substance on neurofibromin action in surviving cells.

5. The method of claim 4, further comprising the step of determining survival of said neurons in media containing a neurotrophin and no candidate substance as a control.

6. The method of claim 4, further comprising the step of determining survival of said neurons in media containing said candidate substance and neurotrophin as a control.

7. The method of claim 4, wherein said neurons are chick neurons.

8. The method of claim 4, wherein said neurons are mouse neurons.

9. The method of claim 4, wherein said neurons are rat neurons.

10. The method of claim 4, wherein said neurons are dorsal root ganglion neurons.

11. The method of claim 4, wherein said neurons are nodose ganglia neurons.

12. The method of claim 4, wherein said neurons are trigeminal ganglia neurons.

13. The method of claim 4, wherein said neurons are sympathetic tunk neurons.

14. The method of claim 4, wherein said neurons are superior cervical neurons.

15. The method of claim 4, wherein said determining comprises measuring neurofibromin transcript levels in surviving cells.

16. The method of claim 4, wherein said determining comprises measuring neurofibromin protein levels in surviving cells.

17. The method of claim 4, wherein said determining comprises measuring p21ras transcript levels in surviving cells.

18. The method of claim 4, wherein said determining comprises measuring p21ras protein levels in surviving cells.

19. The method of claim 4, wherein said determining comprises measuring neurofibromin GTPase activity.

20. The method of claim 4, wherein said determining comprises measuring ratios of active p21ras-GTP to inactive p21ras-GDP.

* * * * *